(12) United States Patent
Mantiuk et al.

(10) Patent No.: US 10,846,832 B2
(45) Date of Patent: Nov. 24, 2020

(54) DISPLAY OF IMAGES

(71) Applicant: Faurecia Irystec Inc., Montreal (CA)

(72) Inventors: Rafal Mantiuk, Bangor (GB); Robert Wanat, Szczecin (PL)

(73) Assignee: Faurecia Irystec Inc., Montreal (CA)

(*) Notice: Subject to any disclaimer, the term of this patent is extended or adjusted under 35 U.S.C. 154(b) by 0 days.

(21) Appl. No.: 16/237,813

(22) Filed: Jan. 2, 2019

(65) Prior Publication Data

US 2019/0272624 A1 Sep. 5, 2019

Related U.S. Application Data

(63) Continuation of application No. 15/318,595, filed as application No. PCT/GB2015/051728 on Jun. 11, 2015, now Pat. No. 10,217,197.

(30) Foreign Application Priority Data

Jun. 13, 2014 (GB) .................................. 1410635.5

(51) Int. Cl.
  *G06T 5/00* (2006.01)
  *A61B 3/024* (2006.01)
(52) U.S. Cl.
  CPC .............. *G06T 5/007* (2013.01); *A61B 3/024* (2013.01); *G06T 2207/20016* (2013.01)
(58) Field of Classification Search
  CPC ....................... G06T 5/007; G06T 2207/20016
  (Continued)

(56) References Cited

U.S. PATENT DOCUMENTS 6,894,720 B2   5/2005 Zhang
7,136,073 B2  11/2006 Newman
            (Continued)

FOREIGN PATENT DOCUMENTS

EP   2992405 A1   3/2016
EP   3026908 A1   6/2016
            (Continued)

OTHER PUBLICATIONS

Mantiuk, R., Mantiuk, R. K., Tomaszewska, A., and Heidrich, W. 2009. Color correction for tone mapping. Computer Graphics Forum (Proc. of Eurographics) 28, 2, 193-202.*
            (Continued)

*Primary Examiner* — Jin Ge
(74) *Attorney, Agent, or Firm* — Occhiuti & Rohlicek LLP

(57) ABSTRACT

The following provides a system and method to display images on a display screen (e.g. via a display panel or by projection) and the processing of image data therefor. In one aspect, the system implements a luminance retargeting method for altering the perceived contrast and/or colours of an image to match their appearance under different luminance levels. In another aspect, the system may provide a method for transforming an image locally within a sub-area of an image to adjust image contrast for display by a display device. In yet another aspect, the system may provide a method for transforming an image of a first luminance to adjust a perceived colour hue thereof for display by a display device according to a second luminance. In yet another aspect, the system may provide a method for transforming an image having a first luminance to adjust a colour saturation thereof for display by a display device having a second luminance.

20 Claims, 11 Drawing Sheets

(58) Field of Classification Search
USPC .......................................................... 345/617
See application file for complete search history.

(56) References Cited

U.S. PATENT DOCUMENTS

| | | | |
|---|---|---|---|
| 8,160,387 | B2 | 4/2012 | Chesnokov |
| 8,330,768 | B2 | 12/2012 | Mantiuk et al. |
| 8,339,475 | B2 | 12/2012 | Atanassov et al. |
| 8,363,131 | B2 | 1/2013 | Lin |
| 8,391,598 | B2 | 3/2013 | Lin |
| 8,456,327 | B2 | 6/2013 | Bechtel et al. |
| 8,463,034 | B2 | 6/2013 | Sambongi et al. |
| 8,483,479 | B2 | 7/2013 | Kunkel et al. |
| 8,831,343 | B2 | 9/2014 | Kunkel et al. |
| 9,092,878 | B2 | 7/2015 | Spitzer et al. |
| 9,299,167 | B2 | 3/2016 | Wan et al. |
| 9,384,561 | B2 | 7/2016 | Romanenko |
| 9,489,920 | B2 | 11/2016 | Tusch |
| 9,747,674 | B2 | 8/2017 | Boitard et al. |
| 9,842,385 | B2 | 12/2017 | Atkins |
| 9,858,677 | B2 | 1/2018 | Romanenko |
| 2006/0002611 | A1 | 1/2006 | Mantiuk et al. |
| 2010/0172411 | A1 | 7/2010 | Efremov et al. |
| 2011/0175925 | A1* | 7/2011 | Kane .................... G01J 1/42 345/589 |
| 2011/0305391 | A1* | 12/2011 | Kunkel ................ H04N 1/6088 382/167 |
| 2013/0321678 | A1* | 12/2013 | Cote ...................... H04N 9/64 348/251 |
| 2013/0322532 | A1 | 12/2013 | Efremov et al. |
| 2015/0178946 | A1* | 6/2015 | Krishnaswamy ........ G06K 9/46 345/582 |
| 2016/0026245 | A1 | 1/2016 | Mantiuk et al. |

FOREIGN PATENT DOCUMENTS

| | | |
|---|---|---|
| PL | 403689 A1 | 10/2014 |
| WO | 2015189629 A2 | 12/2015 |

OTHER PUBLICATIONS

Cao, D., Pokorny, J., Smith, V. C., and Zele, A. J. 2008. Rod contributions to color perception: linear with rod contrast. Vision research 48, 26 (November), 2586-92.*
Jen-Shiun Chiang; Chih-Hsien Hsia; Hao-Wei Peng; Chun-Hung Lien; Hsin-Ting Li, Saturation adjustment method based on human vision with YCbCr color model characteristics and luminance changes, 2012 International Symposium on Intelligent Signal Processing and Communications Systems, Nov. 4-7, 2012.*
J.S. Chiang, C.H. Hsia, et al. Color Image Enhancement with Saturation Adjustment Method. Journal of Applied Science and Engineering, 17(4), pp. 341-352,(2014).*
Michael Ashikhmin, "A Tone Mapping Algorithm for High Contrast Images", Eurographics Workshop on Rendering, 2002, pp. 1-11.
Peter G. J. Barten, "Contrast sensitivity of the human eye and its effects on image quality", HV Press, Knegsel, 1999, pp. 1-225.
C.J. Bartleson and E.J. Breneman, "Brightness Perception in Complex Fields", Journal of the Optical Society of America, Jul. 1967, vol. 57, No. 7, pp. 953-957.
Roy S Berns, "Method for characterizing CRT displays", Elsevier Science B.V., 1996, vol. 16, No. 4, pp. 173-182.
Nuala Brady, David J. Field, " What's Constant in Contrast Constancy? The Effects of Scaling on the Percieved Contrast of Bandpass Patterns", Elsevier Science Ltd., 1995, vol. 35, No. 6, pp. 739-756.
Dingcai Cao, Joel Polorny, Vivianne C. Smith and Andrew J. Zele, "Rod Contributions to Color Perception: Linear with Rod Contrast", National Institute of Health, Nov. 2008, vol. 48, No. 26, pp. 2586-2592.
Naehyuck Chang, Inseok Choi and Hojun Shim, "DLS: Dynamic Backlight Luminance Scaling of Liquid Crystal Display", IEEE Transations on Very Large Scale Integration (VLSI) Systems, Aug. 2004, vol. 12, No. 8, pp. 837-846.
Gabriel Eilertsen, Robert Wanat, Rafal K. Mantiuk and Jonas Unger, "Evaluation of Tone Mapping Operators for HDR-Video", Pacific Graphics, 2013, vol. 32, No. 7, 10 pages.
Fairchild, M.D., "Color Appearance Phenomena", Color Appearance Models, 2nd ed., 1 page.
M.A. Georgeson and G.D. Sullivan, "Contrast Constancy: Deblurring in Human Vision by Spatial Frequency Channels", The Journal of Physicology, 1975, vol. 252, No. 3, pp. 627-656.
Ali Iranli, Wonbok Lee and Massoud Pedram, "Backlight Dimming in Power-Aware Mobile Displays", DAC 2006, vol. 35.4, pp. 604-607.
Louis Kerofsky and Scott Daly, "Brightness preservation for LCD backlight dimming", Journal of the Society for Information Display, 2006, vol. 14/12, pp. 1111-1118.
Adam G. Kirk and James F. O'Brien, "Perceptually Based Tone Mapping for Low-Light Conditions", ACM Transactions on Graphics, Jul. 2011, vol. 30, No. 4, Article 42, pp. 42:1-42:6.
Jiangtao Kuang, Garrett M. John son, Mark D. Fairchild, "iCAM06: A refined image appearance model for HDR image rendering", Journal of Visual Communication & Image Representation, 2007, vol. 18, pp. 406-414.
J.J. Kulikowski, "Effective Contrast Constancy and Linearity of Contrast Sensation", Vision Res., Pergamon Press, 1976, vol. 16, pp. 1419-1431.
Rafal Mantiuk and Hans-Peter Seidel, "Modeling a Generic Tonemapping Operator", The Eurographics Associate and Blackwell Publishing Ltd., 2008, vol. 27, No. 2, 5 pages.
R. Mantiuk, A. Tomaszewska and W. Heidrich, "Color Correction for Tone Mapping", The Eurographics Association and Blackwell Publishing Ltd., 2009, vol. 28, No. 2, 10 pages.
Rafal Mantiuk, Scott Daly, Louis Kerofsky, "Display Adaptive Tone Mapping", 10 pages.
Rafal Mantiuk, Kil Joong Kim, Allan G. Rempel, Wolfgang Heidrich, "HDR-VDP-2: A calibrated visual metric for visibility and quality predictions in all luminance conditions", ACM Transactions on Graphics, Jul. 2011, vol. 30, No. 4, Article 40, pp. 40:1 to 40:13.
Nathan Moroney, Mark D. Fairchild, Robert W.G. Hunt, Changjun Li, M. Ronnier Luo and Todd Newman, "The CIECAM02 Color Appearance Model", IS&T/SID Tenth Color Imaging Conference, pp. 23-27.
Sumanta N. Pattanaik, James A. Ferwerda, Mark D. Fairchild, Donald P. Greenberg, "A Multiscale Model of Adaption and Spatial Vision for Realistic Image Display", Mumsell Color Science Laboratory, Center for Imaging Science, Rocheste Institute of Technology, USA, http://www.cis.rit.edu/people/faculty/fairchild, 12 pages.
Eli Peli, "Contrast in complex images", J. Opt. Soc. Am. A, Oct. 1990, vol. 7, No. 10, pp. 2032-2040.
Adam G. Kirk, James F. O'Brien, "Perceptually Based TOne Mapping for Low-Light Conditions", ACM Transactions on Graphics, Jul. 2011, vol. 30, No. 4, Article 42, pp. 42:1 to 42:9.
Josselin Petit, Rafal K. Mantiuk, "Assessment of video tonemapping: Are cameras' S-shaped tone-curves good enough?", Journal of Visual Communication and Image Representation, 2013, vol. 24, pp. 1020-1030.
Piti Irawan, James A. Ferwerda and Stephen R. Marschner, "Perceptually Based Tone Mapping of High Dynamic Range Image Streams", Eurographics Symposium on Rendering, 2005, 12 pages.
M.J.D. Powell, "An efficient method for finding the minimum of a function of several variables without calculating derivates", Universidade de Vigo, Apr. 28, 2014, pp. 155-162, http://comjnl.oxfordjournals.org/.
Erik Reinhard, Tania Pouli, Timo Kunkel, Ben Long, Anders Ballestad, Gerwin Damberg, "Calibrated Image Appearance Reproduction", ACM Transactions of Graphics, Nov. 2012, vol. 31, No. 6, Article 201, pp. 201:1 to 201:11.
Robert Wanat, Rafal K. Mantiuk, "Simulating and compensating changes in appearance bewteen day and nigh vision", Kodak True Color Image Suite, 12 pages, http://r0k.us/graphics/kodak/.
Vivianne C. Smith and Joel Pokorny, "Spectral Sensitivity of the Foveal Cone Photopigments Between 400 and 500 nm", Vision Res., Pergamon Press, 1975, vol. 15, pp. 161-171.

(56) References Cited

OTHER PUBLICATIONS

William B. Thompson, Peter Shirley and James A. Ferwerda, "A Spatial Post-Processing Algorithm for Images of Night Scenes", Journal of Graphics Tools, 2002, vol. 7. No. 1, pp. 1-12.

J.J. Vos and T.J.T.P. van den Berg, "Vision and Colour Physical Measurement of Light and Raditation", International Commission on Illumination, CIE Collection 1999, pp. 1-9.

Mark D. Fairchild, "Color Appearance Models: Edition 3", John Wiley & Sons, Jun. 7, 2013.

International Search Report and Written Opinion for PCT/GB2015/051728, dated Jan. 22, 2016, 21 pages.

* cited by examiner

DISPLAY OF IMAGES

CROSS-REFERENCED TO RELATED APPLICATIONS

This application is a continuation application of U.S. patent application Ser. No. 15/318,595, filed Dec. 13, 2016, which is a 371 National Stage of International Application No. PCT/GB2015/051728 filed on Jun. 11, 2015 which claims priority to GB Patent Application No. 1410635.5 filed on Jun. 13, 2014, the entire contents of which are incorporated herein by reference.

FIELD OF THE INVENTION

The invention relates to the display of images on a display screen (e.g. via a display panel or by projection) and the processing of image data therefor.

BACKGROUND

The visual acuity of the eye may be measured by asking a subject to distinguish images of objects such as letters or shapes placed upon a white background. Such tests are often employed in assessing corrective lenses such as eye glasses or contact lenses. Objects within an image can typically be better distinguished from the image background if they have a distinctive luminance or colour relative to the background. For example, the relative differences in luminance can be expressed in terms of a quantity known in the art as a 'contrast ratio', or simply 'contrast'. This is typically defined in terms of the difference between two luminance values divided by their sum.

Generally speaking, objects that are difficult to observe relative to their background will have a small contrast. It has been found by experiment that the eye is unable to detect objects within an image when the contrast of the object is below a threshold value, often referred to as the 'contrast detection threshold', or 'contrast threshold'. The reciprocal of this minimum perceivable contrast is often referred to as the 'contrast sensitivity' of the eye.

In the past, in order to investigate and quantify contrast sensitivity, test images containing test patterns have been used. These have often included sinusoidal test patterns comprising a sinusoidal luminance variation extending in one dimension across the image to form stripes of continuously varying (rising and falling) luminance. For such luminance test patterns, contrast is defined simply as the amplitude of the sinusoid divided by the (uniform) mean value of the sinusoid. The threshold amount of contrast required in such a pattern for it to be reliably detected/perceived (e.g. sufficient to give a 50% detection probability) is therefore known as the contrast threshold. The contrast threshold of such a test pattern is dependent upon the wavelength of sinusoidal variation in the image (i.e. the spatial separation, transverse to the stripes, between successive luminance peaks). The reciprocal of this wavelength is known as the 'spatial frequency' of the pattern. Contrast sensitivity may also be measured using a non-sinusoidal luminance variation, and in such cases contrast may be defined as the difference between the maximum and minimum luminance in an image, divided by the sum of them. This is known a 'Michelson contrast'.

Models for various aspects of contrast sensitivity exist in the prior art for 'photopic' luminance conditions—i.e. luminance conditions at daylight vision. These models are based on certain assumptions about the functioning of the human eye. They provide mathematical expressions for quantifying the contrast sensitivity of the eye. A central idea of such models is an assumption that contrast sensitivity is determined by noise in the visual system.

In practice, it has been found that there is not a fixed contrast threshold below which a contrast pattern cannot be detected at all, and above which the contrast pattern can always be detected. Rather, there exists a gradually increasing contrast detection probability. The contrast threshold is typically defined as the contrast at which a 50% probability of detection will exist. A contrast value that is lower than the contrast threshold would be detected with less than 50% probability. The mathematical function that describes the contrast detection probability as a function of contrast strength is generally known as the 'psychometric function'. The statistical factors that determine the shape of the psychometric function are generally considered to be caused by noise, a part of which is internal to the visual system. One example of a psychometric function that has been successfully used in this context is a Normal probability integral which is a cumulative probability distribution function of well-known form, based on a Gaussian ("Normal") probability density function centred on the contrast threshold value. It is a function of the value of the image contrast in question, and it rises continuously from a probability of 0.0 when that contrast is 0.0 to a value asymptotically approaching 1.0 as the contrast increases, passing through a value of 0.5 when the contrast is equal to the contrast threshold.

Experiments suggest that, under photopic conditions, the appearance of the apparent/perceived/visual contrast of two sinusoidal patterns (patterns 1 and 2) is perceived to be equal (i.e. to match) when the true/physical contrast values (C) of the images in question actually differ by the difference in their respective contrast thresholds ($C^T$), such that:

$$C_1 - C_2 = C_1^T - C_2^T$$

This means that:

$$C_1 - C_1^T = C_2 - C_2^T$$

Therefore, the sensation evoked by physical contrast C is generally considered to be a function of its visual contrast ($C - C^T$). The visual contrast in a sinusoidal image, at least, is considered always to be reduced, relative to its true/physical contrast, by the contrast threshold and is proportional to the true/physical contrast of the image.

Luminance levels in images play an important role in the perceived contrast of objects within that image. An image/scene viewed under differing luminance conditions is found to be perceived differently. The same physical scene seen in bright sunlight and in dusky conditions does not appear identical to the human eye. Similarly, images shown on a bright image display and on a relatively lower luminance cinema screen also differ significantly in their appearance.

Colour and contrast perception varies significantly across the range of illumination levels. The most dramatic change in vision is observed when luminance drops below 3-5 cd/m$^2$, when the retinal cone cells steadily lose their sensitivity and visual signal is influenced by the retinal rod cells. In this, so called, 'mesopic' vision range, a gradual loss of acuity and colour vision occurs. This important characteristic of the visual system is rarely taken into account when reproducing colours on electronic displays. While the state-of-the-art display colourimetry is almost entirely based on the cone-mediated vision (CIE colour matching functions), a significant portion of the colour gamut in modern displays often lies in the luminance range below 3 cd/m$^2$, which is partly mediated by rods. This is especially relevant for mobile phone displays, which can decrease their brightness down to 10-30 cd/m² of the peak luminance to reduce power consumption. This means that in the case of a high contrast display that is dimmed, about ¾ of the perceived colour gamut cannot be accurately reproduced using traditional cone-based colorimetry.

The invention aims to address these limitations in the prior art particularly, though not exclusively, in relation to mesopic vision.

SUMMARY OF INVENTION

The following, in one aspect, implements a luminance retargeting method for altering the perceived contrast and/or colours of an image to match their appearance under different luminance levels. The invention preferably employs a psychophysical method of matching contrast. The method may take account of rod-contribution (photoreceptor) to vision. The retargeting preferably involves finding an optimal tone-curve, and/or preferably spatial contrast processing, and/or preferably adjustment of colour hue and/or colour saturation in an image to be displayed. This permits an image to be adjusted or provided that reliably simulates night vision in bright conditions, or to compensate for a bright image shown on a darker display so that it reveals details and/or colours that would otherwise be invisible.

In a second aspect, the following may provide a method for transforming an image locally within a sub-area of an image to adjust image contrast for display by a display device, comprising: calculating a contrast adjustment factor for adjusting a contrast within a sub-area of an original image; and, transforming a contrast within said sub-area of the original image according to the contrast adjustment factor thereby to provide a transformed image for display by said display device; wherein said calculating includes determining a measure of local contrast within said sub-area and therewith determining a contrast adjustment factor that optimises a match between said contrast of said original image and said contrast of said transformed image within said sub-area.

In a third aspect, the following may provide a method for transforming an image of a first luminance to adjust a perceived colour hue thereof for display by a display device according to a second luminance, the method comprising: calculating a colour adjustment factor for adjusting colour values of an original image; and, adjusting said colour values of the original image according to the colour adjustment factor thereby to provide a transformed image for display by the display device at the second luminance; and wherein the calculating includes representing numerically a cone photoreceptor response to the colour values in terms of a corresponding contributory rod photoreceptor response to luminance.

In a fourth aspect, the following may provide a method for transforming an image having a first luminance to adjust a colour saturation thereof for display by a display device having a second luminance, the method comprising: calculating a colour saturation adjustment transform for adjusting colour values of an original image; and, adjusting the colour values ($\tilde{X}$) of the original image according to the colour saturation transform thereby to provide a transformed image for display by the display device at the second luminance; wherein a the adjusted colour value is defined according to the value of the first luminance (Y) and the value of the second luminance ($\tilde{Y}$) and a saturation correction factor (s( . . . )) in accordance with the following transform:

$$\hat{X} = \tilde{Y} \times \left(\frac{\tilde{X}}{\tilde{Y}}\right)^{s(Y)/s(\tilde{Y})}$$

in which the saturation correction factor is a function of luminance and approaches a value of zero as the value of luminance approaches zero and monotonically approaches a value of one (1.0) asymptotically as luminance increases. This unusual form, of tending to zero as a function of falling luminance, has been found by experiment and has proved to be surprisingly effective in colour saturation correction.

In a fifth aspect, the following may provide apparatus for transforming an image for display by a display device according to a peak luminance for display, the apparatus comprising: a calculating unit for calculating a tone curve which maps luminance levels of an original image to luminance levels of the transformed image; and, a transforming unit for transforming luminance levels of the original image according to the tone curve thereby to provide a transformed image for display by said display device; wherein the calculating unit is arranged to determine the tone curve that optimises a match between a contrast of the original image and a contrast of the transformed image.

In a sixth aspect, the following may provide an apparatus for transforming an image to adjust image contrast locally within a sub-area of an image for display by a display device comprising: a calculating unit for calculating a contrast adjustment factor for adjusting a contrast within a sub-area of an original image; and, a transforming unit for transforming a contrast within said sub-area of the original image according to the contrast adjustment factor thereby to provide a transformed image for display by the display device; wherein the calculating unit is arranged to determine a measure of local contrast within the sub-area and therewith determine a contrast adjustment factor that optimises a match between the contrast of the original image and the contrast of the transformed image within the sub-area.

In a seventh aspect, the following may provide an apparatus for transforming an image of a first luminance to adjust a perceived colour hue thereof for display by a display device according to a second luminance, the apparatus comprising: a calculating unit for calculating a colour adjustment factor for adjusting colour values of an original image; and, an adjuster unit for adjusting the colour values of the original image according to the colour adjustment factor thereby to provide a transformed image for display by the display device at the second luminance; wherein the calculating unit is arranged to represent numerically a cone photoreceptor response to the colour values in terms of a corresponding contributory rod photoreceptor response to luminance.

In its eighth aspect, the following may provide apparatus for transforming an image having a first luminance to adjust a colour saturation thereof for display by a display device having a second luminance, the method comprising: a calculating unit for calculating a colour saturation adjustment transform for adjusting colour values of an original image; and, an adjuster unit for adjusting the colour values ($\tilde{X}$) of the original image according to the colour saturation transform thereby to provide a transformed image for display by the display device at the second luminance; wherein the adjuster unit is arranged to adjust a said colour value according to the value of the first luminance (Y) and the value of the second luminance ($\tilde{Y}$) and a saturation correction factor (s( . . . )) according to the following transform:

$$\hat{X} = \tilde{Y} \times \left(\frac{\tilde{X}}{\tilde{Y}}\right)^{s(Y)/s(\tilde{Y})}$$

in which the saturation correction factor is a function of luminance and approaches a value of zero as the value of luminance approaches zero and monotonically approaches a value of one (1.0) asymptotically as luminance increases.

In a further aspect, the following may provide an apparatus for performing a method described above.

In a yet further aspect, the following may provide a computer program or computer program product comprising computer-executable instructions arranged to implement a method according to an aspect described above, when executed in a computer. The invention may provide a computer programmed to implement a method according to an aspect described above.

In yet another aspect, the following may provide a method for adjusting data for an image for display by a display device according to ambient lighting conditions, the method comprising: providing first luminance data representing first luminance levels of pixels of an image suitable for display under a first ambient lighting; providing second luminance data representing luminance levels of pixels of said image which are different to said first luminance data and are suitable for display under a second ambient lighting different from said first ambient lighting; adjusting luminance levels of the first luminance data such that an image contrast within the whole image represented by the adjusted first luminance data substantially matches a corresponding image contrast within the whole image represented by the second luminance data; determining a background luminance within the whole image represented by the adjusted first luminance data; defining an image sub-region within the image and adjusting luminance levels of the first luminance data associated with the image sub-region such that an image contrast local to the image sub-region substantially matches a corresponding image contrast local to image sub-region as represented by second luminance data of the image; generating luminance image data using said background luminance and the adjusted first luminance data of the image sub-region for use in displaying said image under said second ambient lighting.

In yet another aspect, the following may provide a method for transforming an image for display by a display device according to a peak luminance for display, the method comprising: calculating a tone curve which maps luminance levels of an original image to luminance levels of the transformed image; and transforming luminance levels of the original image according to the tone curve thereby to provide a transformed image for display by said display device; wherein said calculating includes determining the tone curve that optimises a match between an observer sensitivity and/or adaptivity to contrast at a luminance level for said original image and an observer sensitivity and/or adaptivity to contrast at a luminance level for said transformed image.

In yet another aspect, the following may provide a method for transforming an image to adjust image contrast locally within a sub-area of an image for display by a display device comprising: calculating a contrast adjustment factor for adjusting a contrast within a sub-area of an original image; and, transforming a contrast within said sub-area of the original image according to the contrast adjustment factor thereby to provide a transformed image for display by said display device; wherein said calculating includes determining a measure of local contrast within said sub-area and therewith determining a contrast adjustment factor that optimises a match between an observer sensitivity and/or adaptivity to contrast at a luminance level for said original image and an observer sensitivity and/or adaptivity to contrast at a luminance level for said transformed image within said sub-area.

BRIEF DESCRIPTION

Figure 1:
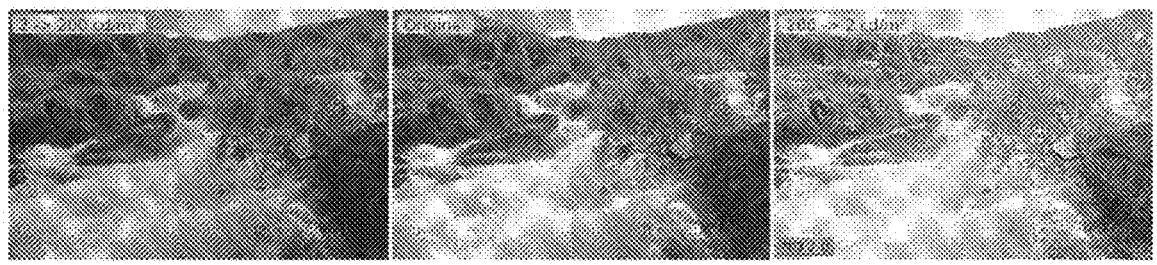
FIG. 1 illustrates an original image (centre) and two retargeted images (left; right)

As noted above, in one aspect, the following implements a luminance retargeting method for altering the perceived contrast and/or colours of an image to match their appearance under different luminance levels. The invention preferably employs a psychophysical method of matching contrast. In preferred embodiments the invention may take account of rod-contribution (photoreceptor) to vision. The retargeting preferably involves finding an optimal tone-curve, and/or preferably spatial contrast processing, and/or preferably adjustment of colour hue and/or colour saturation in an image to be displayed. This permits an image to be adjusted or provided that reliably simulates night vision in bright conditions, or to compensate for a bright image shown on a darker display so that it reveals details and/or colours that would otherwise be invisible.

To account for changes in image appearance due to a lower absolute luminance level, the invention preferably implements a new appearance matching methodology and luminance retargeting methodology. The method may be used to compensate for appearance changes between luminance levels, which allows for further reduction in display brightness and hence power saving. The method may also be used to perform retargeting in the opposite direction, from dark scenes to much brighter displays, in order to reproduce the appearance of night scenes. The method preferably takes account of colour and contrast perception across the entire range of luminance. A change of overall brightness and contrast may be compensated preferably by optimizing the shape of a tone-curve so that it provides a better compromise between retaining contrast and brightness while utilizing the available dynamic range of a display. The change in detail visibility may be accounted for using a novel visual contrast matching method. The change of colour appearance may preferably be accounted for by representing rod contributions and loss of colour saturation at low luminance levels. Each of these components individually or in combination preferably provide superior appearance matching across a range of luminance, which cannot be achieved with the existing methods.

In a first aspect, the invention may provide a method for transforming an image for display by a display device according to a peak luminance for display, the method comprising: calculating a tone curve which maps luminance levels of an original image to luminance levels of the transformed image; and, transforming luminance levels of the original image according to the tone curve thereby to provide a transformed image for display by said display device; wherein the calculating includes determining the tone curve that optimises a match between a contrast of the original image and a contrast of the transformed image in which the peak luminance of the tone curve does not exceed the peak luminance of the transformed image for display by the display device.

In this way, an appropriately constrained tone curve may be used form the mechanism to calculate and apply a contrast adjustment to an image. The calculating of the tone curve may be performed on a piecewise basis in which the tone curve is represented as a piecewise linear function with a plurality of linear sections each representing a specific range of tones and in which the determination of that linear section is performed according to the above optimization process. Once all linear sections of the tone curve are calculated, then so too is the complete tone curve covering all relevant tones. The tone curve may be rendered effectively/practically non-linear, if desired, by making the linear sections sufficiently small in extend and large in number to approximate a continuous curve, however this may be more computationally burdensome.

The contrast of the original image is preferably a visual contrast value being the difference between a "physical" contrast value for the original image and a detection threshold contrast value for the original image. For example, two contrasts being matched according to the above optimization may each be defined by the general form:

$$\text{Visual Contrast} = C - C^T$$

where C is a physical contrast numerical value, which is a property of the image, and $C^T$ is a contrast detection threshold numerical value. It is found to be most effective to apply the optimization technique in respect of visual contrasts. Accordingly, preferably, the contrast of the transformed image is also a visual contrast value being the difference between a physical contrast value for the transformed image and a detection threshold contrast value for the transformed image. Consequently, the optimising a match preferably includes minimising a difference between a visual contrast of the original image and a visual contrast of the transformed image. The purpose of the optimization is, in general terms, to achieve a closest suitable approximation to the condition:

$$C_1 - C_1^T = C_2 - C_2^T$$

or, $$(C_1 - C_1^T) - (C_2 - C_2^T) = \Delta = 0$$

In respect of images 1 (original) and 2 (transformed).

The optimising a match may include minimising a sum of the squared differences between a visual contrast of the original image and a visual contrast of the transformed image in respect of a plurality of different luminance values within the original image. For example, because it may not be possible to achieve a perfect match between the contrasts being matched, for all luminance levels relevant to the tone curve being calculated, one may find that the closest numerical approximation to a perfect match ($\Delta=0$) may be a value of $\Delta$ that fluctuates between positive and negative small values over the range of luminance being considered for the tone curve. By optimising the sum of the squared values of the all those fluctuations ($\Sigma \Delta^2$) to be as small as possible one may effectively optimise collectively across a range of luminance for a tone curve.

The optimizing may be implemented as a minimization/optimization of:

$$\left(G - G_t(l) - \frac{dT}{dl} G + G_t(T(l))\right)^2$$

or of:

$$\underset{T(l)}{\operatorname{argmin}} \int_{l_{min}}^{l_{max}} S(l) \left(G - G_t(l) - \frac{dT}{dl} G + G_t(T(l))\right)^2 dl$$

or of:

$$\underset{T(l)}{\operatorname{argmin}} \int_{l_{min}}^{l_{max}} S(l) \left(G - G_t(l) - \frac{dT}{dl} G + G_t(T(l))\right)^2 + \tau(l - T(l))^2 dl$$

This may be preferably subject to:

$$\frac{dT}{dl} \geq 0$$

And preferably also subject to:

$$T(l_{min}) \geq d_{min}, \quad T(l_{max}) \leq d_{Max}$$

Where $G_t(l)$ is the threshold contrast and $T(l)$ is the tone curve to be determined, for log-luminance l. The term τ is a constant which may be between 0.001 and 0.00001 (e.g. about 0.0001). Also, $l_{min}$ and $l_{max}$ are the minimum and maximum values of luminance within the original image, and $d_{min}$ and $d_{max}$ are the minimum and maximum values of luminance within the transformed image for display by the display device (e.g. the limits set by the display device).

The detection threshold contrast value for the original image and/or the transformed image is preferably defined by a predetermined contrast sensitivity function which is a function of luminance and spatial frequency. The detection threshold contrast value $M_t$ may be defined as:

$$M_t = \frac{\Delta L}{L} = \frac{1}{S \cdot CSF(\rho, L_a)}$$

Here, "S" is the absolute sensitivity factor which is preferable to adjust the absolute threshold for a particular experimental scenario. The value of S in preferred embodiments may be between 8.0 and 9.0, most prefersbly S=8.6, or thereabouts. The threahold contrsst value may be defined in log-luminance space via:

$$G_t(l) = \frac{1}{2}\log_{10}\left(\frac{M_t + 1}{1 - M_t}\right),$$

with contrast generally being $$G(l) = \frac{1}{2}\log_{10}\left(\frac{M + 1}{1 - M}\right)$$

There are many contrast sensitivity functions (CSF) known in the art and the skilled reader may select appropriately, however, it has been found that a CSF of the following form is effective:

$$CSF(\rho) = p_4 s_A(l) \frac{MTF(\rho)}{\sqrt{(1 + (p_1 \rho)^{p_2})(1 - e^{-(\rho/7)^2})^{-p_3}}}$$

in which the modulation transfer function (MTF) which models the visual effects/impact upon contrast sensitivity caused by the scattering of light by/within the eye, may be defined as a function of image spatial frequency (ρ) as;

$$MTF(\rho) = \sum_{k=1...4} a_k e^{-b_k \rho}$$

and the joint luminance sensitivity curve for cone and rod photoreceptors may be given by;

$$s_A(l) = p_5\left(\left(\frac{p_6}{l}\right)^{p_7} + 1\right)^{-p_8}$$

Figure 3:
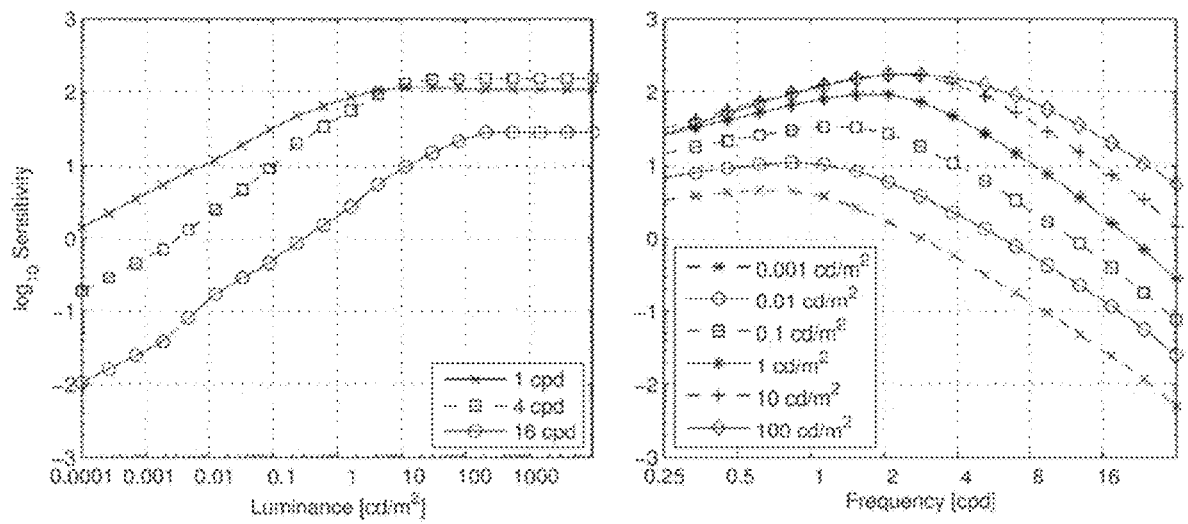
FIG. 3 illustrates two Contrast Sensitivity Functions (CFS) according to image luminance (left) and image spatial frequency (right)

The variable ρ is spatial frequency (cycles per degree) and l is logarithmic luminance ($l = \log_{10}(Y)$) where Y is a luminance value. The parameters $p_1$ to $p_8$ and $a_1$ to $a_4$ are fitting parameters that may be selected by the user as according to preference. However, an example of this CSF is shown in FIG. 3 herein, and it is discussed in detail in:

MANTIUK, R., KIM, K. J., REMPEL, A. G., AND HEIDRICH, W. 2011. HDR-VDP-2: *A calibrated visual metric for visibility and quality predictions in all luminance conditions.* ACM Trans. Graph (Proc. SIGGRAPH) 30, 4 (July 2011), 1.

Examples of numerical values for these parameters are as follows.

MTF—Modulation Transfer Function of the Eye

| k | $a_k$ | $b_k$ |
|---|-------|-------|
| 1 | 0.424839 | 0.028 |
| 2 | 0.572435 | 0.37 |
| 3 | 0.000167576 | 37 |
| 4 | 0.00255872 | 360 |

CSF—(Neural) Contrast Sensitivity Function

| Adapting luminance $L_a$ [cd/m²] | $p_1$ | $p_2$ | $p_3$ | $p_4$ |
|---|---|---|---|---|
| 0.002 | 0.991265 | 3.74038 | 0.50722 | 4.46044 |
| 0.02 | 0.800889 | 3.54104 | 0.682505 | 4.94958 |
| 0.2 | 0.476505 | 4.37453 | 0.750315 | 5.28678 |
| 2 | 0.405782 | 4.40602 | 0.935314 | 5.61425 |
| 20 | 0.334278 | 3.79542 | 1.07327 | 6.4635 |
| 150 | 0.394533 | 2.7755 | 1.16577 | 7.45665 |

Values of the parameters $p_1$ to $p_4$ employed in the CSF are given above, and are the functions of luminance ($L_a$). To get values for $p_1$-$p_4$ for a given luminance, one may interpolate (in log-luminance space) between the tabulated values.

$s_A$—Joint Luminance Sensitivity

| $p_5$ | $p_6$ | $p_7$ | $p_8$ |
|---|---|---|---|
| 30.162 | 4.0627 | 1.6596 | 0.2712 |

An alternative to the CSF is Barten's CSF from:
BARTEN, P. G. J. (1999). Contrast sensitivity of the human eye and its effects on image quality (p. 208). SPIE Press.

The calculating preferably includes transforming luminance levels (Y) of both the original image and the transformed image into logarithmic luminance values (l) defined according to $l = \log_{10}(Y)$, and calculating the tone curve in respect of the logarithmic luminance levels. This has advantages numerically. For example, models expressed in terms of logarithmic contrast values do not suffer from singularities at high contrast values.

Furthermore, the slope of a tone curve in the logarithmic domain corresponds to a contrast change. Preferably, this property is exploited such that the calculating may include representing the contrast of the transformed image as the product of the contrast of the original image and a value of the slope of the tone curve in respect of a given luminance. This simplifies the process of calculating the optimal tone curve.

The invention in its first aspect may thus provide a way of adjusting image contrast globally to optimise the visual contrast of the image according to the maximum luminance of a tone (maximum value of the tone curve) at which the adjusted image is to be displayed by a display device. This may be of particular use when modifying images initially intended/prepared for viewing on a bright image display/screen, such that they can be optimally viewed on darkened displays, such as is more suitable in low-light surroundings. A well-selected tone curve can greatly improve the appearance of the modified/transformed image. However, in a second aspect, the invention may provide a method of transforming local features of an image which takes account of the contrast levels and spatial frequencies of the image in local regions individually. This local transformation technique may be applied alone, or in conjunction with the image transformation techniques of the invention in its first aspect—i.e. as a combined process for transforming an image both globally and locally.

In the second aspect, the invention may provide a method for transforming an image locally within a sub-area of an image to adjust image contrast for display by a display device, comprising: calculating a contrast adjustment factor for adjusting a contrast within a sub-area of an original image; and, transforming a contrast within said sub-area of the original image according to the contrast adjustment factor thereby to provide a transformed image for display by said display device; wherein said calculating includes determining a measure of local contrast within said sub-area and therewith determining a contrast adjustment factor that optimises a match between said contrast of said original image and said contrast of said transformed image within said sub-area wherein the luminance in said sub-area of the original image does not match the luminance in said sub-area of the transformed image for display by the display device.

In this way, a local contrast-matching methodology is provided in which local contrast may be measured. The measure of local contrast may be in terms of a measure of local variation (e.g. variance or standard deviation) of pixel luminance levels within a defined local area, and this may be used to optimise a match of contrasts of original and transformed images within the local area. For example, the match optimisation may be performed on a pixel-by-pixel level, in which a measure of local contrast is determined for a pixel within a given local area in terms of the local variation of luminance within that area in relation to the pixel. The measure of local contrast may be any suitable measure of contrast or luminance variation as would be readily apparent to the skilled person (e.g. using an existing definition of contrast, or in terms of variance or standard deviation in luminance values, within a defined local area, or using the values provided by the decomposition into the Laplacian (difference-of-Gaussians) pyramid).

Preferably, the contrast of the original image is also a visual contrast value being the difference between a physical contrast value for the original image and a detection threshold contrast value for the original image. Preferably, the contrast of the transformed image is also a visual contrast value being the difference between a physical contrast value for the transformed image and a detection threshold contrast value for the transformed image. Consequently, the optimising a match preferably includes minimising a difference between a visual contrast of the original image and a visual contrast of the transformed image. The contrast adjustment factor is preferably determined such that the difference between the value of the measure of local contrast (e.g. c) and the value of the product (e.g. c—m) of the measure of local contrast and the adjustment factor (e.g. m), substantially matches the difference between the detection threshold contrast value (e.g. $\overline{G}_t$) for the transformed image and the detection threshold contrast value (e.g. $G_t$) for the original image.

The detection threshold contrast value for the original image and/or said transformed image is preferably defined by a predetermined contrast sensitivity function which is a function of luminance and spatial frequency. There are many contrast sensitivity functions (CSF) known in the art and the skilled reader may select appropriately, however, it has been found that a CSF of the following form is effective:

$$CSF(\rho) = p_4 s_A(l) \frac{MTF(\rho)}{\sqrt{(1+(p_1\rho)^{p_2})(1-e^{-(\rho/7)^2})^{-p_3}}}$$

in which the modulation transfer function (MTF) which models the visual effects/impact upon contrast sensitivity caused by the scattering of light by/within the eye, may be defined as a function of image spatial frequency ($\rho$) as;

$$MTF(\rho) = \sum_{k=1\ldots 4} a_k e^{-b_k \rho}$$

and the joint luminance sensitivity curve for cone and rod photoreceptors may be given by;

$$s_A(l) = p_5 \left(\left(\frac{p_6}{l}\right)^{p_7} + 1\right)^{-p_8}$$

The variable $\rho$ is spatial frequency (cycles per degree) and l is logarithmic luminance ($l=\log_{10}(Y)$) where Y is a luminance value. The parameters $p_1$ to $p_8$ and $a_1$ to $a_4$ are fitting parameters that may be selected by the user as according to preference.

The detection threshold contrast value $M_t$ may be defined as:

$$M_t = \frac{\Delta L}{L} = \frac{1}{S \cdot CSF(\rho, L_a)}$$

Here, "S" is the absolute sensitivity factor which is preferable to adjust the absolute threshold for a particular experimental scenario. The value of S in preferred embodiments may be between 8.0 and 9.0, most prefersbly S=8.6, or thereabouts. The threahold contrsst value may be defined in log-luminance space via:

$$G_t(l) = \frac{1}{2} \log_{10}\left(\frac{M_t + 1}{1 - M_t}\right),$$

with contrast generally being $$G(l) = \frac{1}{2}\log_{10}\left(\frac{M+1}{1-M}\right)$$

Values of the parameters $p_1$ to $p_4$ employed in the CSF are given above, and are the functions of luminance ($L_a$). To get values for $p_1$-$p_4$ for a given luminance, one may interpolate (in log-luminance space) between the tabulated values.

The sub-area is preferably defined by a spatial window function centred thereupon in which the width of the window function is proportional to the inverse of a spatial frequency of the original image such that the width of the window function is smaller for higher spatial frequencies.

The spatial window function may be any suitable window function such as would be readily apparent to the skilled person. The spatial window function may be zero-valued outside of the defined sub-area. It may be bell-shaped, rectangular or triangular for example, or other shape. Examples include the two-dimensional Gaussian window function, a Parzen window function, or a Hamming window function, or other spatial window function. For example, a two-dimensional Gaussian window function $g_\sigma$ may be applied to a spatial function $f(x,y)$ (e.g. luminance image: $f(x,y)=l(x,y)$) in the following manner:

$$g_\sigma * f(x,y) = f(x-u_1, y-u_2) G_\sigma(u_1) G_\sigma(u_2) du_1 du_2$$

where, for $i=1, 2$, the Gaussian function defining the window and having standard deviation $\sigma$, is expressed as:

$$G_\sigma(u_i) = \frac{1}{\sqrt{2\pi\sigma^2}} \exp(-u_i^2/\sigma^2)$$

The function G could be another window function, other than a Gaussian. The measure of local contrast (c) may be determined in respect of the luminance (l) of pixel values according a spatial window function (g) defining said sub-area and centred thereupon (x, y) according to:

$$c(x,y) = \sqrt{g*[l(x,y)-g*l(x,y)]^2}$$

wherein the operator (*) is the convolution operator. The spatial window function may be a Gaussian kernel with the standard deviation $\sigma$. The Gaussian window may be controlled/adjusted to get smaller for higher spatial frequencies to account for finer scale. This may be achieved by making it equal to half of the size of a single cycle at a particular spatial frequency:

$$\sigma = 0.5 \frac{R_{ppd}}{\rho}$$

where $R_{ppd}$ is the angular display resolution of a display for displaying the image, in pixels per visual degree, and $\rho$ is the spatial frequency in cycles per degree.

The calculating preferably includes transforming luminance levels (Y) of both the original image and the transformed image into logarithmic luminance values (l) defined according to $l=\log_{10}(Y)$ and calculating said adjustment factor in respect of said logarithmic luminance levels.

The image to be transformed may be decomposed into a plurality of component images each one of which corresponds to an aforesaid original image above and may be individually processed as such. Accordingly, the calculating preferably includes decomposing the original image into an image pyramid which comprises a plurality of different component images which each represent the original image via spatial frequencies within a respective one of a plurality of different spatial frequency bands. The calculating of an adjustment factor may comprise calculating a respective adjustment factor for some or each component image. The transforming may comprise transforming some or each component image, and may further comprise recomposing a transformed image from a plurality of the transformed component images. For example, the method may include decomposing an image into a difference-of-gaussians (Laplacian) image pyramid, then manipulating pixel values of each image pyramid level so that the visual contrast of a given original pyramid-level image and the visual contrast of the corresponding transformed pyramid-level image substantially match, and then recomposing/reconstructing the transformed image using the transformed pyramid-level images.

The contrast adjustment factor may be implemented as:

$$m_k(x, y) = \frac{c_k(x, y) - G(M_t) + G(\tilde{M}_t)}{c_k(x, y)}$$

where $c_k(x, y)$ is the contrast at the pixel location (x, y) and k-th level of the image pyramid where $k=1 \ldots N$. The value of N may be selected such that the coarsest band (optionally, except the base band) has the peak frequency less or equal to 2 cpd.

Contrast adjustment as a local enhancement of an image (e.g. Laplacian) pyramid may be implemented as:

$$\tilde{P}_k(x,y) = P_k(x,y) \cdot m_k(x,y) \qquad (17)$$

where $P_k$ corresponds to the original image pyramid level. Of course, in other embodiments no image pyramid is employed in which case the above expressions may be implemented by setting $N=1$ and $P_{k=1}$ corresponds to the original image level (no pyramid).

The method may further include substituting the component image associated with the lowest spatial frequencies with a background luminance (e.g. base-band image) derived from within the original image as transformed according to the invention in its first aspect. For example, a base-band of a transformed image according to the invention in its first aspect, may be used to reconstruct an image using the transformed pyramid-level images. The calculating preferably includes representing the contrast of the transformed image or transformed component image according to (e.g. as) the product of the contrast of the original image and the value of the adjustment factor.

In the third aspect, the invention may provide a method for transforming an image of a first luminance to adjust a perceived colour hue thereof for display by a display device according to a second luminance, the method comprising: calculating a colour adjustment factor for adjusting colour values of an original image; and, adjusting said colour values of the original image according to the colour adjustment factor thereby to provide a transformed image for display by the display device at the second luminance; wherein the calculating includes representing numerically a cone photoreceptor response to the colour values in terms of a corresponding contributory rod photoreceptor response to luminance, and wherein the cone photoreceptor response per unit luminance at the second luminance is constrained to substantially match the cone photoreceptor response per unit luminance at the first luminance. The contributory rod photoreceptor response is preferably a luminance-dependent value added to the cone photoreceptor response.

The step of representing numerically a cone photoreceptor response preferably includes separately representing the individual responses of L-cones, M-cones and S-cones each in terms of a respective corresponding contributory rod photoreceptor response to luminance. Preferably, the colour values are trichromatic colour values, such as RGB colour values.

In this way, for example, colour adjustment may comprise converting an original image into cone and 30 rod responses, then calculating the rod contribution to the long-wavelength (visible light), medium-wavelength (visible light) and short-wavelength (visible light) cone responses depending upon the second luminance, and adding the rod contribution to the long-wavelength, medium-wavelength and short-wavelength cone responses.

The photoreceptor responses (L, M, S) of each cone channel ($E_L$, $E_M$, $E_S$) may be expressed with an additive term representing the rod input to that cone signal channel caused a rod photoreceptor response $E_R$.

For example:

$L = E_L + k_0 E_R$ $M = E_M + k_1 E_R$ $S = E_S + k_2 E_R$

Here, $k_i$ (i=0, 1, 2) are weighting factors. Preferably the weighting factors are luminance-dependent (Y). Preferably, $k_0 = k_1$. Preferably, $k_2$ differs from $k_0$ and $k_1$. For example, when $k_0 = k_1$, the values of the weighting factors are luminance dependent as follows:

| Y [cd/m$^2$] | 10 | 0.62 | 0.10 |
|---|---|---|---|
| $k_1$ | 0 | 0.0173 | 0.173 |
| $k_2$ | 0 | 0.0101 | 0.357 |

The responses to the original and transformed images are preferably normalized by the luminance of the transformed image or the original image respectively, and the normalized responses to the transformed images are adjusted to match the normalized responses to the original. The resulting matched, normalized transformed image responses are then converted back to RGB values.

In the fourth aspect, the invention may provide a method for transforming an image having a first luminance to adjust a colour saturation thereof for display by a display device having a second luminance, the method comprising: calculating a colour saturation adjustment transform for adjusting colour values of an original image; and, adjusting the colour values ($\tilde{X}$) of the original image according to the colour saturation transform thereby to provide a transformed image for display by the display device at the second luminance; wherein a the adjusted colour value is defined according to the value of the first luminance (Y) and the value of the second luminance ($\tilde{Y}$) and a saturation correction factor (s( . . . )) in accordance with the following transform:

$$\hat{X} = \tilde{Y} \times \left(\frac{\tilde{X}}{\tilde{Y}}\right)^{\frac{s(Y)}{s(\tilde{Y})}}$$

in which the saturation correction factor is a function of luminance and approaches a value of zero as the value of luminance approaches zero and monotonically approaches a value of one (1.0) asymptotically as luminance increases. This unusual form, of tending to zero as a function of falling luminance, has been found by experiment and has proved to be surprisingly effective in colour saturation correction.

The colour values ($\tilde{X}$) are preferably trichromatic colour values, such as RGB.

The method may include determining an average luminance of the original image having the first luminance and determining an average luminance of the image having the first luminance, determining a respective value of the saturation correction factor (s( . . . )) according to each said average luminance and adjusting the colour values using the respective values of the saturation correction factor.

The original image may be an image adjusted or transformed according to the method of the invention in its first or second aspect. Thus, the invention may provide a colour saturation adjustment method including determining a colour saturation correction in respect of an original image, determining a colour saturation correction in respect of a contrast-transformed image according to the invention in its first or second aspect, applying the colour saturation correction to pixel colour values according to the ratio of the saturation correction in respect of the original image due to the luminance thereof and the saturation correction in respect of the contrast-transformed image due to the luminance thereof.

The original image may be an image adjusted or transformed according to the method of the invention in its third aspect. Thus, the colour saturation correction may be applied to a colour-hue corrected original image.

The above colour processing may not only improve colour match, but may also reduce the bluishness of images when seen in darkness. This is desirable for two reasons. First, it puts less strain on rods, which are very sensitive to blue. Second, such images interfere less with the photosensitive Retinal Ganglion Cells, which are responsible for day-night cycle clock in our brain. Some attribute cases of insomnia to the abundance of bluish light in TV and mobile devices, which people use in the evening. These are two added benefits of the invention in its relevant aspects.

In the fifth aspect, the invention may provide apparatus for transforming an image for display by a display device according to a peak luminance for display, the apparatus comprising: a calculating unit for calculating a tone curve which maps luminance levels of an original image to luminance levels of the transformed image; and, a transforming unit for transforming luminance levels of the original image according to the tone curve thereby to provide a transformed image for display by said display device; wherein the calculating unit is arranged to determine the tone curve that optimises a match between a contrast of the original image and a contrast of the transformed image in which the peak luminance of the tone curve does not exceed the peak luminance of the transformed image for display by the display device.

The contrast of the original image is preferably a visual contrast value being the difference between a physical contrast value for the original image and a detection threshold contrast value for the original image.

The contrast of the transformed image is preferably a visual contrast value being the difference between a physical contrast value for said transformed image and a detection threshold contrast value for said transformed image.

The calculating unit is preferably arranged to perform the step of optimising a match by a process including minimising a difference between a visual contrast of the original image and a visual contrast of the transformed image.

The calculating unit may be arranged to perform the step of optimising a match by a process including minimising a sum of the squared differences between a visual contrast of the original image and a visual contrast of the transformed image in respect of a plurality of different luminance values within the original image.

The detection threshold contrast value for the original image and/or the transformed image is preferably defined by a predetermined contrast sensitivity function which is a function of luminance.

The calculating unit is preferably arranged to transform luminance levels (Y) of both the original image and the transformed image into logarithmic luminance values (l) defined according to $l=\log_{10}(Y)$ and to calculate the tone curve in respect of the logarithmic luminance levels.

The calculating unit may be arranged to calculate the contrast of the transformed image as the product of the contrast of the original image and a value of the slope of the tone curve in respect of a given luminance.

In the sixth aspect, the invention may provide an apparatus for transforming an image to adjust image contrast locally within a sub-area of an image for display by a display device comprising: a calculating unit for calculating a contrast adjustment factor for adjusting a contrast within a sub-area of an original image; and, a transforming unit for transforming a contrast within said sub-area of the original image according to the contrast adjustment factor thereby to provide a transformed image for display by the display device; wherein the calculating unit is arranged to determine a a measure of local contrast within the sub-area and therewith determine a contrast adjustment factor that optimises a match between the contrast of the original image and the contrast of the transformed image within the sub-area wherein the luminance in said sub-area of the original image does not match the luminance in said sub-area of the transformed image for display by the display device.

The calculating unit is preferably arranged to determine the contrast adjustment factor such that the difference between the value of the measure of local contrast and the value of the product of the measure of local contrast and the adjustment factor, substantially matches the difference between the detection threshold contrast value for the transformed image and the detection threshold contrast value for the original image.

The calculating unit is preferably arranged to define the sub-area by a spatial window function centred thereupon (x, y) in which the width of the window function is proportional to the inverse of a spatial frequency of the original image such that the width of the window function is smaller for higher spatial frequencies.

The calculating unit may be arranged to determine the measure of local contrast (c) in respect of the luminance (l) of pixel values according a spatial window function (g) defining the sub-area and centred thereupon (x, y) according to:

$$c(x,y)=\sqrt{g*[l(x,y)-g*l(x,y)]^2}$$

wherein the operator (*) is the convolution operator.

The calculating unit may be arranged to define the detection threshold contrast value for the original image and/or said transformed image by a predetermined contrast sensitivity function which is a function of luminance and spatial frequency.

The calculating unit is preferably arranged to transform luminance levels (Y) of both the original image and the transformed image into logarithmic luminance values (l) defined according to $l=\log_{10}(Y)$ and to calculate the adjustment factor in respect of the logarithmic luminance levels.

The image to be transformed may be decomposed into a plurality of component images each one of which corresponds to an aforesaid original image above and may be individually processed as such. Accordingly, the calculating unit is preferably arranged to decompose the original image into an image pyramid which comprises a plurality of different component images which each represent the original image via spatial frequencies within a respective one of a plurality of different spatial frequency bands. The calculating unit is preferably arranged to calculate the adjustment factor by a process comprising calculating a respective adjustment factor for some or each component image. The transforming unit is preferably arranged to transform some or each component image, and may further me arranged to recompose a transformed image from a plurality of the transformed component images.

The calculating unit is preferably arranged to substitute the component image associated with the lowest spatial frequencies with a background luminance (e.g. base-band image) derived from within the original image as transformed by the apparatus in its fifth aspect. The calculating unit may be arranged to represent the contrast of the transformed image as the product of the contrast of the original image and the value of the adjustment factor.

In the seventh aspect, the invention may provide an apparatus for transforming an image of a first luminance to adjust a perceived colour hue thereof for display by a display device according to a second luminance, the apparatus comprising: a calculating unit for calculating a colour adjustment factor for adjusting colour values of an original image; and, an adjuster unit for adjusting the colour values of the original image according to the colour adjustment factor thereby to provide a transformed image for display by the display device at the second luminance; wherein the calculating unit is arranged to represent numerically a cone photoreceptor response to the colour values in terms of a corresponding contributory rod photoreceptor response to luminance, and to constrain the cone photoreceptor response per unit luminance at the second luminance to substantially match the cone photoreceptor response per unit luminance at the first luminance.

The contributory rod photoreceptor response is preferably a luminance-dependent value represented as an addition to the cone photoreceptor response.

The calculating unit is preferably arranged to represent numerically a cone photoreceptor response by separately representing the individual responses of L-cones, M-cones and S-cones each in terms of a respective corresponding contributory rod photoreceptor response to luminance. The photoreceptor responses (L, M, S) of each cone channel ($E_L$, $E_M$, $E_S$) may be expressed with an additive term representing the rod input to that cone signal channel caused a rod photoreceptor response $E_R$. For example:

$$L=E_L+k_0 E_R$$

$$M=E_M+k_1 E_R$$

$$S=E_S+k_2 E_R$$

Here, $k_i$ (i=0, 1, 2) are weighting factors. Preferably the weighting factors are luminance-dependent (Y). Preferably, $k_0=k_1$. Preferably, $k_2$ differs from $k_0$ and $k_1$. For example, when $k_0=k_1$, the values of the weighting factors are luminance dependent as follows:

| Y [cd/m$^2$] | 10 | 0.62 | 0.10 |
|---|---|---|---|
| $k_1$ | 0 | 0.0173 | 0.173 |
| $k_2$ | 0 | 0.0101 | 0.357 |

The colour values are preferably trichromatic colour values.

In its eighth aspect, the invention may provide apparatus for transforming an image having a first luminance to adjust a colour saturation thereof for display by a display device having a second luminance, the method comprising: a calculating unit for calculating a colour saturation adjustment transform for adjusting colour values of an original image; and, an adjuster unit for adjusting the colour values ($\tilde{X}$) of the original image according to the colour saturation transform thereby to provide a transformed image for display by the display device at the second luminance; wherein the adjuster unit is arranged to adjust a said colour value according to the value of the first luminance (Y) and the value of the second luminance ($\tilde{Y}$) and a saturation correction factor (s( . . . )) according to the following transform:

$$\hat{X} = \tilde{Y} \times \left(\frac{\tilde{X}}{\tilde{Y}}\right)^{\frac{s(Y)}{s(\tilde{Y})}}$$

in which the saturation correction factor is a function of luminance and approaches a value of zero as the value of luminance approaches zero and monotonically approaches a value of one (1.0) asymptotically as luminance increases.

The colour values ($\tilde{X}$) are preferably trichromatic colour values, e.g. RGB.

The calculating unit may be arranged to determine an average luminance of the original image having the first luminance and to determine an average luminance of the image having the first luminance, and to determine a respective value of the saturation correction factor (s( . . . )) according to each said average luminance and to adjust said colour values using the respective values of the saturation correction factor.

In a further aspect, the invention may provide an apparatus for performing a method described above.

In a yet further aspect, the invention may provide a computer program or computer program product comprising computer-executable instructions arranged to implement a method according to an aspect described above, when executed in a computer. The invention may provide a computer programmed to implement a method according to an aspect described above.

In yet another aspect, the invention may provide a method for adjusting data for an image for display by a display device according to ambient lighting conditions, the method comprising: providing first luminance data representing first luminance levels of pixels of an image suitable for display under a first ambient lighting; providing second luminance data representing luminance levels of pixels of said image which are different to said first luminance data and are suitable for display under a second ambient lighting different from said first ambient lighting; adjusting luminance levels of the first luminance data such that an image contrast within the whole image represented by the adjusted first luminance data substantially matches a corresponding image contrast within the whole image represented by the second luminance data; determining a background luminance within the whole image represented by the adjusted first luminance data; defining an image sub-region within the image and adjusting luminance levels of the first luminance data associated with the image sub-region such that an image contrast local to the image sub-region substantially matches a corresponding image contrast local to image sub-region as represented by second luminance data of the image; generating luminance image data using said background luminance and the adjusted first luminance data of the image sub-region for use in displaying said image under said second ambient lighting.

The step of determining a background luminance may comprise extracting a base band of luminance data from the adjusted first luminance data of the whole image.

The adjusting of luminance levels of the first luminance data preferably includes adjusting a tone curve associated with the whole image such that the adjusted first luminance data substantially matches a corresponding image contrast within the whole image represented by the second luminance data.

The step of extracting a base band may be performed after the tone curve is adjusted and after the substantial matching of image contrast within the whole image is performed.

The method may include providing colour components associated with the first luminance data. The method may include determining an adjustment to the hue thereof using the first luminance data, the second luminance data and the colour components. The method may further include applying the hue adjustment to the colour components to provide adjusted colour components for use with the adjusted first luminance data of the image sub-region for use in displaying the image under said second ambient lighting.

The hue adjustment is preferably determined numerically using at least one numerical value representing a response of a cone photoreceptor which is defined according to a numerical value representing a response of a rod photoreceptor.

The step of adjusting luminance levels of the first luminance data associated with the image sub-region may include decomposing the first data into a plurality of representations of the image each at a different respective spatial resolution (e.g. according to a Laplacian pyramid). The step of generating luminance image data may include replacing with the background luminance a said representation of the image which has the lowest spatial resolution from amongst the representations.

DETAILED DESCRIPTION OF DRAWINGS

Method and Visual Models

Figure 2:
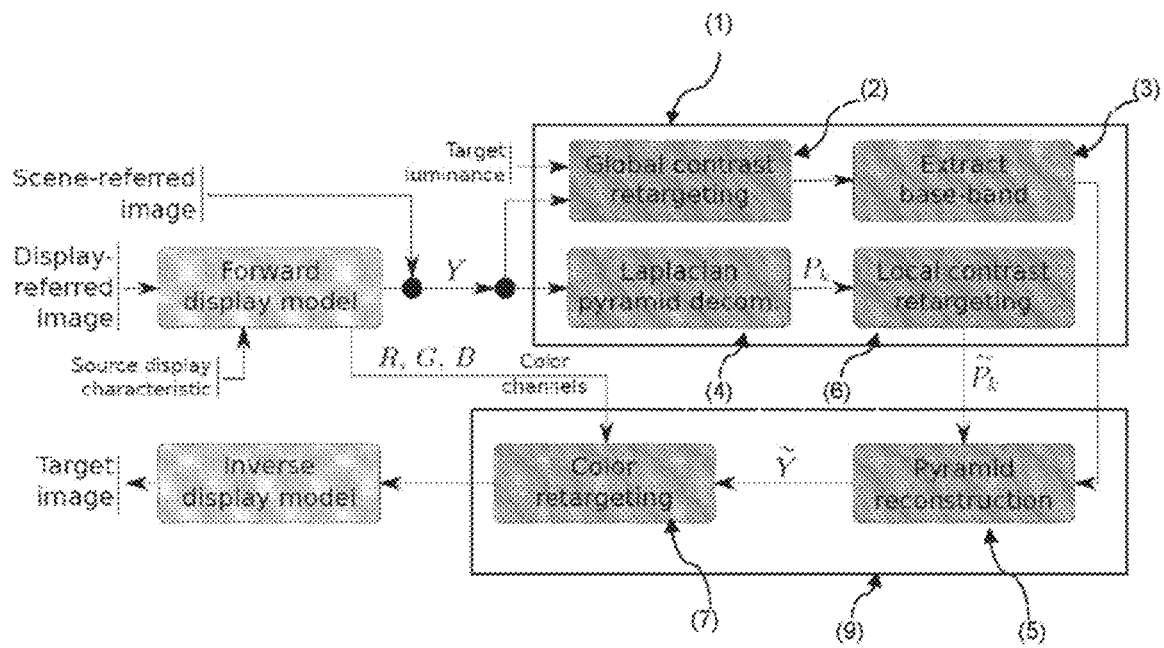
FIG. 2 illustrates a schematic flow diagram for a retargeting method according to a preferred embodiment of the invention.

As shown in FIG. 2, input to the methods of a preferred embodiment of the invention is eitthodher a scene-referred image (a high dynamic range image, represented in absolute units), or a display referred-image, for example in the sRGB colour space.

In the latter case, the image needs to be transformed from gamma corrected pixel values into absolute linear RGB values using a display model, such as a gamma-offset-gain (GOG) model [Berns 1996]. Similarly, the retargeted result of the present method may be transformed to pixel values using an inverse display model, or alternatively, into the sRGB colour space. To model complex interaction between the absolute luminance level and image appearance, we analyse the problem with respect to three different aspects of an image: global contrast (tone-curve), local contrast (detail), and colour. The following sections discuss each aspect in detail.

FIG. 1 shows examples of the result of applying the present methods according to this preferred embodiment. Retargeting from and to a dark display is shown. FIG. 1, left: This is an image as seen on a 2 cd/m² peak luminance display. FIG. 1, centre: The original image. FIG. 1, right: This is a bright image compensated for a 2 cd/m² display. When the original image is seen through a neutral density filter reducing luminance 100 times (2.0D), or on a display in which the backlight is dimmed to $\frac{1}{100}^{th}$ of the original luminance, it will match the appearance of the left image. When the right image is seen through the same filter thus simulating a dark display, it will appear similar to the original. Note that the seemingly exaggerated sharpness, colour shift and brightness change are not perceived as such at low luminance levels. The images are best seen when the page is enlarged to ¾th of the screen width and viewed from about 0.5 m for a 24" monitor.

Referring to FIG. 2, there is shown schematically an apparatus comprising a calculating unit (1) and a transforming unit (9). The calculating unit (1) comprises a global contrast retargeting unit (2) arranged to receive as input both a luminance image (Y) to be transformed, and a target luminance in respect of which the input image is to be transformed—that is to say, the contrast and/or colour of the input image are to be transformed to render the resultant image better for viewing at the target luminance level.

Optionally, but preferably, a base-band image extractor unit (3) is provided as shown (but may be omitted) and is arranged to receive the output of the global contrast retargeting unit and to extract a base-band image therefrom. In such an embodiment, the calculating unit also includes a Laplacian pyramid decomposition unit (4) which is arranged to receive as input the luminance image (Y) to be transformed, and to decompose that image into a Laplacian image pyramid, comprising a plurality of pyramid levels of differing spatial frequency intervals, The output of the base-band extractor unit and the output of the Laplacian pyramid decomposition unit are both arranged to be input to a transforming unit (9). In preferred embodiments, the transforming unit comprises a pyramid reconstruction unit (5) which is arranged to reconstruct an image from the pyramid levels received from the pyramid decomposition unit. The pyramid decomposition unit may be arranged to do so using all of the received pyramid levels except the one having the lowest spatial frequency range, and to substitute in its place the base-band image delivered to it from the base-band extractor unit. In this way, all but one of the pyramid levels, plus the base-band image, may be used by the pyramid reconstruction unit to reconstruct a transformed image which may be output for display. In other embodiments the transforming unit may omit the pyramid reconstruction unit and may simply output the global contrast-re-targeted image from the global contrast retargeting unit, for display.

In preferred embodiments, the calculating unit also comprises a local contrast retargeting unit (6) arranged to receive as input the Laplacian pyramid image levels output by the Laplacian pyramid decomposition unit, and to apply local contrast retargeting thereto, as discussed below, and to output the locally contrast-retargeted image pyramid levels to the pyramid reconstruction unit for reconstruction as described above.

In some embodiments, the calculating unit may comprise (either alone or together with other units described above and/or illustrated in FIG. 2) a colour retargeting unit (7) arranged to receive as input the colour channels (e.g. RGB) of an image to be transformed according to the colour transformation methods described herein, and to output the result for display. The colour retargeting unit is arranged to concurrently receive a luminance image (Y) which is either output directly from the global contrast retargeting unit, or the pyramid reconstruction unit (as shown), or is simply an original image to be colour transformed without being subject to contrast transformation. Alternatively, the colour retargeting unit may be present in the transforming unit (as shown) when both colour retargeting and global contrast retargeting is desired, in which case the output of the global contrast retargeting unit would be input to the colour retargeting unit. Alternatively, the colour retargeting unit and the pyramid reconstruction unit may both be present in the transforming unit when both colour retargeting and local and/or global contrast retargeting is desired (as shown), in which case the output of the pyramid reconstruction unit would be input to the colour retargeting unit.

The input luminance image data and colour channel data may be initially "display-referred" data requiring adjustment to remove/invert the bespoke characteristics associated with the display device they have been provided by (if, indeed, that is the source of the data). In this sense, for example, so-called R'G'B'L' data may be adjusted according to a suitable "forward display model" (8) to RGBL data for subsequent transformation according to the present invention. Once so transformed, the RGBL data may be adjusted as required to account for the bespoke characteristics associated with the display device via which image display is to take place, such that RGBL→R'G'B'L'.

In this way, one may implement the global contrast retargeting method of the present invention, and/or the local contrast retargeting method, and/or one or both of the colour retargeting methods. FIG. 2 shows, for clarity, the situation where all retargeting methods are applied, in a preferred embodiment.

Contrast Retargeting

Before discussing contrast matching models, let us introduce two measures of contrast that we will use in this section. The Michelson contrast is defined as:

$$M = \frac{L_{max} - L_{min}}{L_{max} + L_{min}} = \frac{\Delta L}{L_{mean}} \qquad (1)$$

where $L_{max}$ and $L_{min}$ are the maximum and minimum luminance values of a sine wave, or alternatively $\Delta L$ is the modulation and $L_{mean}$ is the mean value of a sine wave. The Michelson contrast varies between 0 and 1.

When calculating image contrast in a multi-scale representation, such as a Laplacian pyramid, it is more convenient to use the logarithmic contrast:

$$G = \frac{1}{2}\log_{10}\left(\frac{L_{max}}{L_{min}}\right) \qquad (2)$$

The logarithmic contrast can be interpreted as the modulation of the sine wave in the logarithmic domain. We will use G and M symbols in the rest of the paper to distinguish between both measures. The following equations convert from one contrast to another:

$$G(M) = \frac{1}{2}\log_{10}\left(\frac{M+1}{1-M}\right), \quad M(G) = \frac{10^{2G}-1}{10^{2G}+1} \quad (3)$$

Our ability to see small contrast (sensitivity) varies greatly with both frequency of the stimulus and its luminance. Such variations are well described by a number of Contrast Sensitivity Functions (CSFs) [Baden 1999], such as the one shown in FIG. 3. In FIG. 3, a Contrast Sensitivity Function (CSF) is shown in terms of its variation with luminance (left) and spatial frequency (right). The function is based on the model from [Mantiuk et al. 2011]. The frequency is given in cycles per degree (cpd).

The plots show the variation in sensitivity, which is the inverse of the threshold detection contrast. Although the CSF captures an essential characteristic of the visual system, it does not explain the perception of contrast in complex images. This is because the CSF predicts visibility of very small, almost invisible contrast, presented on a uniform background, which is atypical for most complex scenes. The variations in contrast perception are much smaller for contrast sufficiently above the detection threshold. This was shown by George son and Sullivan [1975], who measured the magnitude of contrast of one frequency that matches the magnitude of contrast of another frequency. They found that the lines of matching contrast across spatial frequencies range from a strongly bent curve for low contrast, which closely corresponds to the CSF, to an almost flat line for supra-threshold contrast. Georgeson and Sullivan coined the expression "contrast constancy" for the notion of the invariability of supra-threshold contrast across viewing conditions.

There is ample evidence that contrast constancy holds across the frequency range both for narrow-band patterns, such as sine-waves [Baden 1999] and for broadband patterns, such as bandpass-noise [Brady and Field 1995]. Brady and Field [1995] reported that contrast matches are almost perfect once the contrast is above the detection threshold without any gradual transition between near threshold and supra-threshold vision. This, however, cannot be said about the contrast matches across the luminance range, where significant deviations from contrast constancy can be observed even for relatively large contrast magnitudes [Kulikowski 1976]. Therefore, we need to assume that the contrast constancy mechanism behaves differently in the frequency and luminance domains. Kulikowski [1976] observed that, over a wide range of parameters, two contrast magnitudes match in their appearance when their visual contrast matches. That implies that the physical contrast M minus the detection threshold $M_t$ must be equal for matching contrast:

$$M - M_t = \tilde{M} - \widetilde{M_t} \quad (4)$$

where M and $\tilde{M}$ are Michelson contrasts seen at different luminance. The detection threshold $M_t$ is predicted by the CSF function:

$$M_t = \frac{\Delta L}{L} = \frac{1}{S \cdot CSF(\rho, L_a)} \quad (5)$$

where $\rho$ is the spatial frequency in cycles per degree and $L_a$ is the background luminance in cd/m². In the present considerations we preferably employ the CSF from [Mantiuk et al. 2011]. S is the absolute sensitivity factor, which may optionally be used to adjust the absolute thresholds for a particular experimental scenario. Using the present parameter adjustment experimental setup, we determined that S=8.6 produces good matches. The peak sensitivity at 100 cd/m² for this S-value is $M_t$=0.4%, which is consistent with most CSF measurements.

Although the Kulikowski model was defined in terms of Michelson contrast, it is convenient to formulate matching contrast in terms of the logarithmic contrast:

$$G - G_t = \tilde{G} - \widetilde{G_t}, \text{ where } G_t = G(M_t) \quad (6)$$

Figure 4:
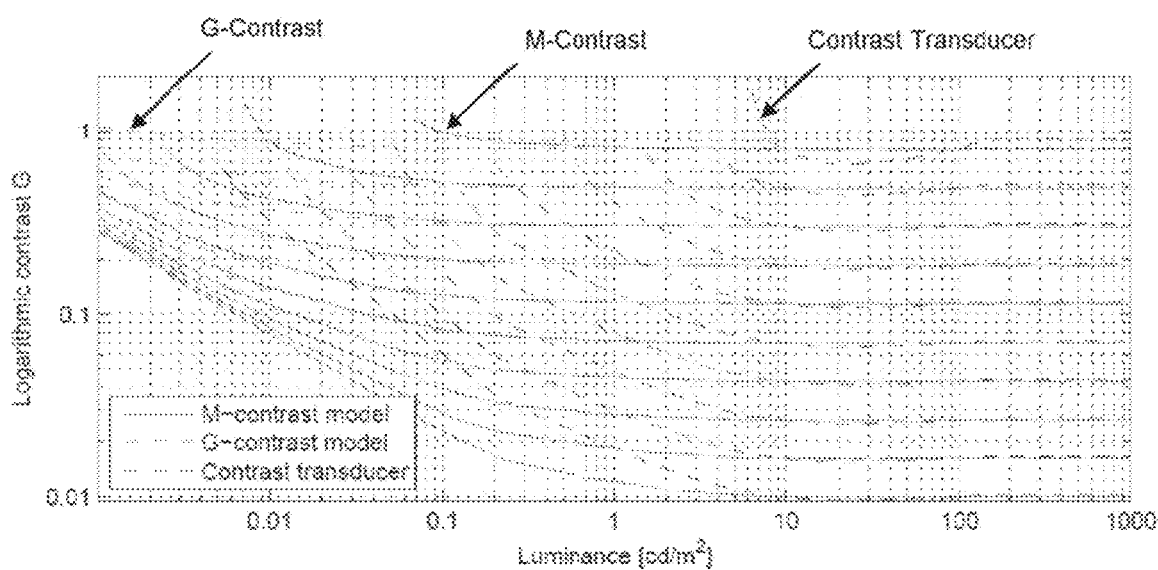
FIG. 4 illustrates a graph showing lines of matching contrast magnitude as a function of luminance.

Note that Eq. 6 is not equivalent to Eq. 4 due to a non-linear relation between the contrast measures. However, as shown in FIG. 4, matching contrast lines are almost identical for both models, except for very high contrast and low luminance. Because data does not exist for such high contrast levels, neither model can be said to be right or wrong. We will use the logarithmic contrast in the present model because it does not suffer from singularities at high contrast.

FIG. 4 also reveals an important characteristic of this contrast matching model. The lines of matching contrast magnitude are shown as a function of luminance. The lines join the contrast values that should appear the same according to the model. Lines of matching contrast are more curved for low contrast, which means that low contrast is more affected by luminance than high contrast. This is contrary to another popular model of supra-threshold contrast: contrast transducer [Pattanaik et al. 1998; Mantiuk et al. 2008]. The transducer predicts a much larger increase of physical contrast, regardless of the contrast magnitude. Such prediction is inconsistent with the experimental data.

Figure 6:
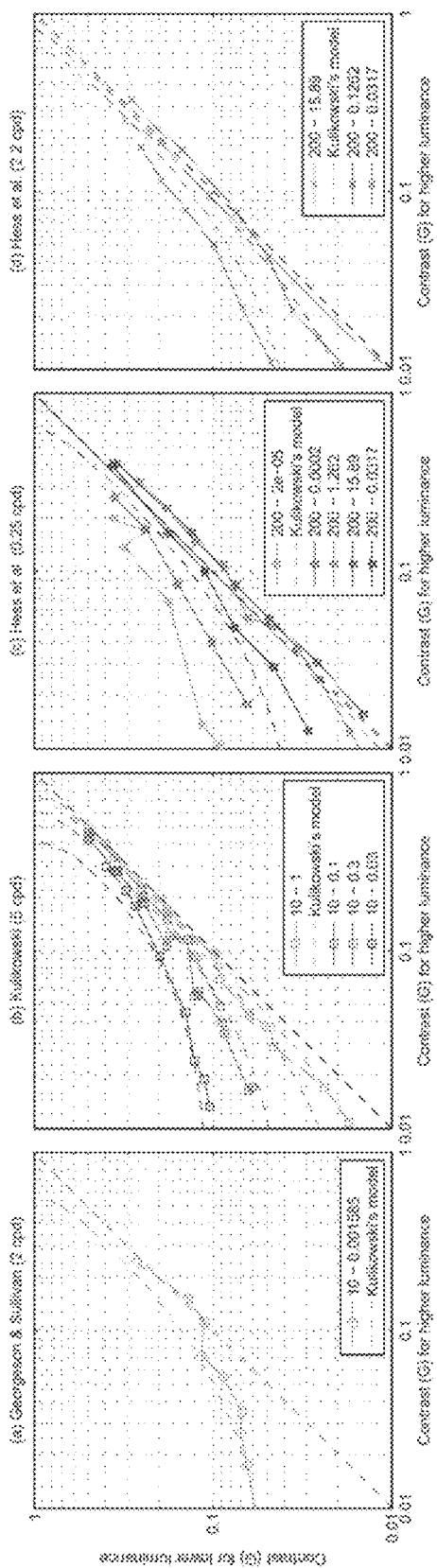
FIG. 6 illustrates contrast matching data according to four different contrast matching methods.

Despite its simplicity, the model proposed by Kulikowski accurately predicts experimental data. In FIG. 6 we collected contrast matching data from several sources and compared them with the model predictions. FIG. 6 shows contrast matching data from several sources (continuous lines) and Kulikowski's model prediction. Different line styles denote different pairs of test and reference luminance (in cd/m2) as listed in the legends, with the contrast of the higher luminance plotted on the x-axis. Even when we used the same CSF for all the data sets, the model could predict that the physical contrast at low luminance has to be increased to match the appearance of contrast at high luminance just as indicated by an amount indicated by measurements. Kulikowski's model compares favourably to alternative models of perceived contrast, such as contrast transducer, models of brightness perception, JND luminance scaling, which all formed the lines very far from the data points (not included in the plot for better clarity). The model also encompasses our everyday experience of seeing in low light. The objects do not appear more blurry at night, as predicted by the multiplicative sensitivity loss in the aforementioned models. Instead their silhouettes are sharp but their textures lose low contrast details.

Global Contrast

A tone curve is a powerful tool for reshaping image appearance. It can adjust perceived contrast in two ways: directly, by changing its slope, and, in the case of low luminance, indirectly by changing brightness of the image parts and their perceived contrast according to the model from Eq. 4. Therefore, contrast can be increased by using a steeper tone-curve (gamma>1), but this tends to make an image darker. Alternatively, a less steep tone-curve could be used (gamma<1) to make the image brighter and perceived contrast higher. In this section, we demonstrate how to find the best compromise between these two potential solutions using Kulikowski's model of matching contrast.

Figure 5:
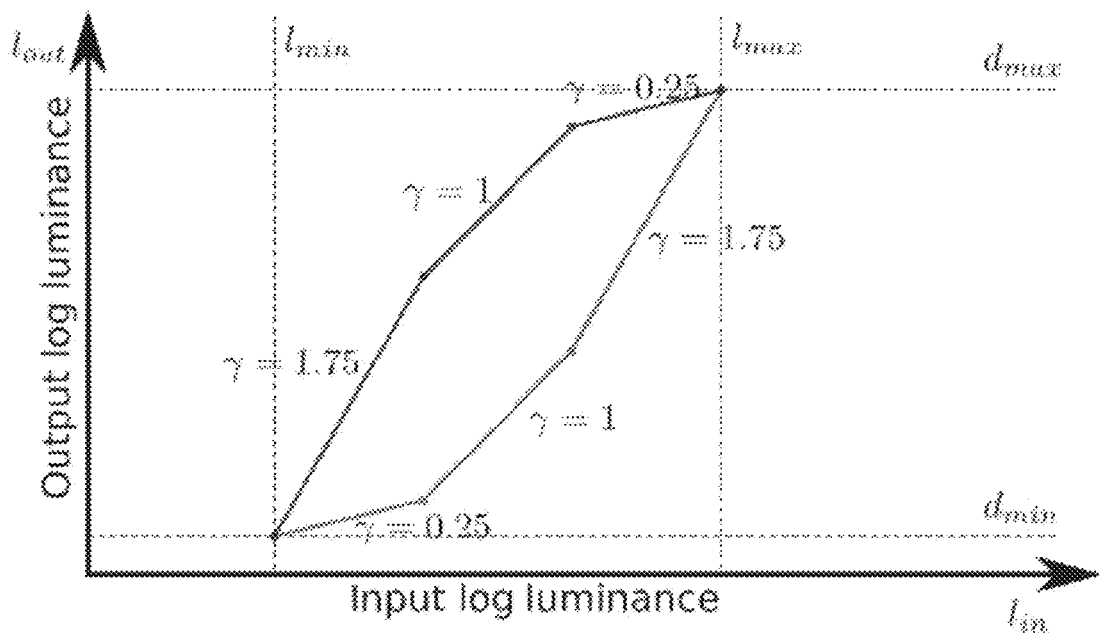
FIG. 5 illustrates two piece-wise linear tone-curves for an image.

Its shape alters both physical and perceived/visual image contrast, where the latter is affected by absolute luminance. To illustrate it, let us assume that any tone curve can be approximated by a piece-wise linear function, such as the lower curve shown in FIG. 5. In FIG. 5, two piece-wise linear tone-curves are shown. The lower curve expands contrast in bright tones and compresses contrast in dark tones. Because the middle tones are pushed towards lower luminance levels, their perceived contrast will be reduced. The opposite is achieved with the upper tone-curve. The slope describes the change of physical contrast. If we use the slope $\gamma=1.75$ to expand contrast in brighter tones, we boost both perceived and physical contrast for these tones. But this also forces us to compress darker tones as the dynamic range of the output display device is limited to the range $d_{min}$–$d_{max}$. Moreover, since middle tones are pushed towards lower luminance, their perceived contrast is lowered, as predicted by the model from Eq. 4. Therefore, in order to boost perceived image contrast, it is necessary to use the opposite tone-curve, such as one shown uppermost in FIG. 5. In this section, we demonstrate how to find a tone-curve that results in optimum perceived contrast given the limitations of the output device.

The task is to find a tone-curve T that maps input luminance to output luminance so that the distortions in perceived contrast are minimized. We find such a curve for a representative contrast G and a spatial frequency $\rho$. For simplicity, the tone-curve T( . . . ) is defined in the log luminance space $$\tilde{l}=T(l), \text{ where } l=\log_{10}(Y) \quad (7)$$

so that the resulting physical contrast can be expressed as:

$$\tilde{G} = \frac{dT}{dl}G \quad (8)$$

The above equation relies on the fact that the slope of a tone-curve in the log domain corresponds to the contrast change. The problem of finding the optimum tone-curve can be expressed as the optimization, where the squared difference of both sides of the Kulikowski's model (Eq. 6) is minimized. Formally, this can be expressed as:

$$\operatorname*{argmin}_{T(l)} \int_{l_{min}}^{l_{max}} S(l)\left(G - G_t(l) - \frac{dT}{dl}G + G_t(T(l))\right)^2 + \tau(l-T(l))^2 dl \quad (9)$$

Subject to:

$$\frac{dT}{dl} \geq 0 \quad (10)$$

and $$T(l_{min}) \geq d_{min}, T(l_{max}) \leq d_{max} \quad (11)$$

$G(l)$ is the threshold contrast for log-luminance l (Eq. 5). The second term of the objective function is the difference between the source (l) and target log luminance (T(l)) and is weighted with a small constant $\tau=0.0001$. The term is necessary to push the tone-curve towards either bright or dark tones when the dynamic range of the target image is lower than the dynamic range of a display. The first constraint (Eq. 10) ensures that the tone-curve is monotonic and increasing. The two remaining constraints (Eq. 11) ensure that the tone-curve does not exceed the minimum and maximum luminance of the target display ($d_{min}$, $d_{max}$). Note that the dynamic range and black level of the display are the parameters of the present method. Therefore, it is possible to adjust results for displays of varying contrast and seen under varying ambient illumination.

The optional saliency function S(l) is used only for high dynamic range images, which may contain small areas that greatly expand the dynamic range but do not form a salient part of an image. In such a case, it is preferred to choose a tone curve that will foremost match the appearance of the areas that form a significant part of the image. This is achieved by assigning weights to different luminance levels during optimization. In the simplest case, the function is a histogram of the input image (i.e. the weight applied to a given luminance is proportional to, or equal to, the height of the histogram column for that luminance level within the luminance histogram of the image—thus, more frequent luminance levels receive higher weight), though it is beneficial to further weight the histogram by a measure of contrast, so that less weight is assigned to large uniform areas. The disadvantage of using the saliency function is that the tone curve can change between frames. Even with some form of temporal filtering, this can lead to temporal colour inconsistencies [Eilertsen et al. 2013]. Therefore, for video processing and the display-referred scenarios, we preferably set all saliency weights to 1.

The above optimization problem can be efficiently solved numerically after converting a tone curve into a discrete piecewise linear function. The quadratic terms of the objective function let us express the problem as quadratic programming with inequality constraints. Because the threshold function $G_t$ introduces nonlinearity, the quadratic problem is preferably solved iteratively, where the threshold function is approximated with its first order Taylor expansion in each iteration. Because there are very few optimized variables (usually about 20-30), the solver is efficient. If no saliency function is used, the solution can be precomputed per pair of source ($l_{min}$, $l_{max}$) and destination ($d_{min}$, $d_{max}$) luminance ranges. For simplicity, we preferably solve this problem for a single representative spatial frequency $\rho=2$ cpd, which approximately corresponds to the peak sensitivity of the visual system for a range of luminance levels (refer to FIG. 3—right), and for a representative contrast G=0.4. These values were found to produce the best matching results using the present experimental setup.

Figure 7:
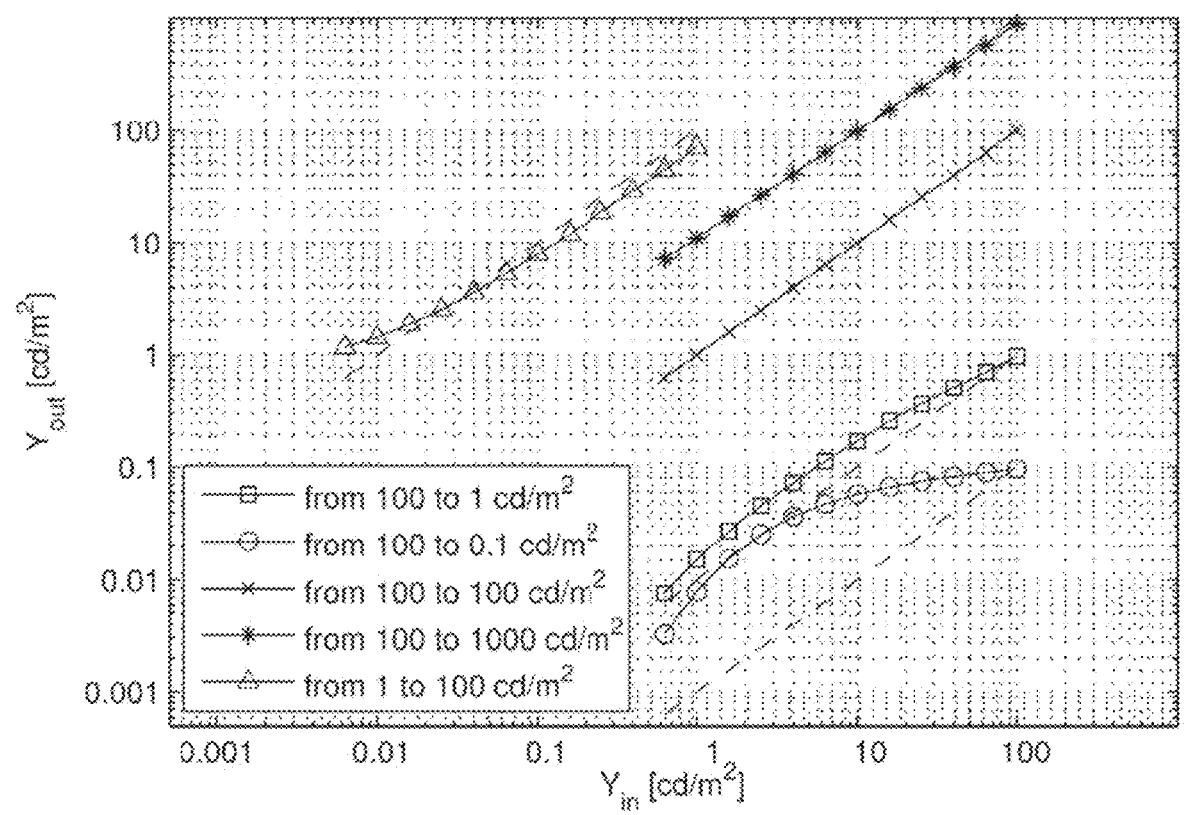
FIG. 7 illustrates tone curves adjusted according to preferred embodiments of the invention for retargeting luminance of an image.

Several tone-curves computed for different source and target luminance levels are shown in FIG. 7. The tone-curves are shown for luminance retargeting that results in minimum perceived contrast distortion. The dashed lines represent linear mapping (gamma=1). Note that, when retargeting from 100 to 1 cd/m2, the tone-curve becomes less steep (gamma<1) for bright tones and more steep for dark tones. This behaviour is very different from a typical gamma=1.5 curve used for "dark" conditions. There is also little change in the shape of the tone-curve when retargeting from 100 to 1000 cd/m$^2$, as the sensitivity (CSF) does not change much above 100 cd/m$^2$. The images produced by tone-curves that were optimized for different retargeting scenarios can be found in the top row of FIG. 8.

Note that, in a preferred embodiment shown in FIG. 2, the tone curve is applied to the full resolution luminance image in the global contrast retargeting step, followed by the extraction of a baseband. It may appear to be more efficient to apply the tone curve to the baseband extracted in the Laplacian pyramid decomposition step. This, however, leads to strong halo artefacts when a nonlinear tone curve is applied to blurred edges in a base-band image.

Local Contrast

A well selected tone curve can hugely improve the appearance of the retargeted image, however, it offers very coarse control over the contrast, limited to the selection of regions of similar luminance. Two other parameters of the contrast matching model, spatial frequency and contrast magnitude, are preferably also addressed on a local level. To achieve local contrast control, a preferred embodiment of the invention is to decompose an image into frequency-selective bands using the Laplacian pyramid (refer to FIG. 2). The pyramid may preferably be computed for the log of luminance values so that the band-pass levels contain logarithmic contrast values (Eq. 2).

While spatial frequency is readily provided by the multi-scale decomposition, estimating contrast magnitude G requires more care. Contrast in complex images is typically estimated from the band pass contrast representation [Peli 1990], which can be extracted from a Laplacian pyramid. However, there are two problems with this approach: a) Contrast is arguably best defined in terms of edges. Detecting edges, however, requires integration of information across several scales (frequency bands) [Witkin 1984]. Therefore, the perceived contrast is not formed by a single frequency band, but by integration of information from a plurality of, or preferably all, frequency bands.

Figure 9:
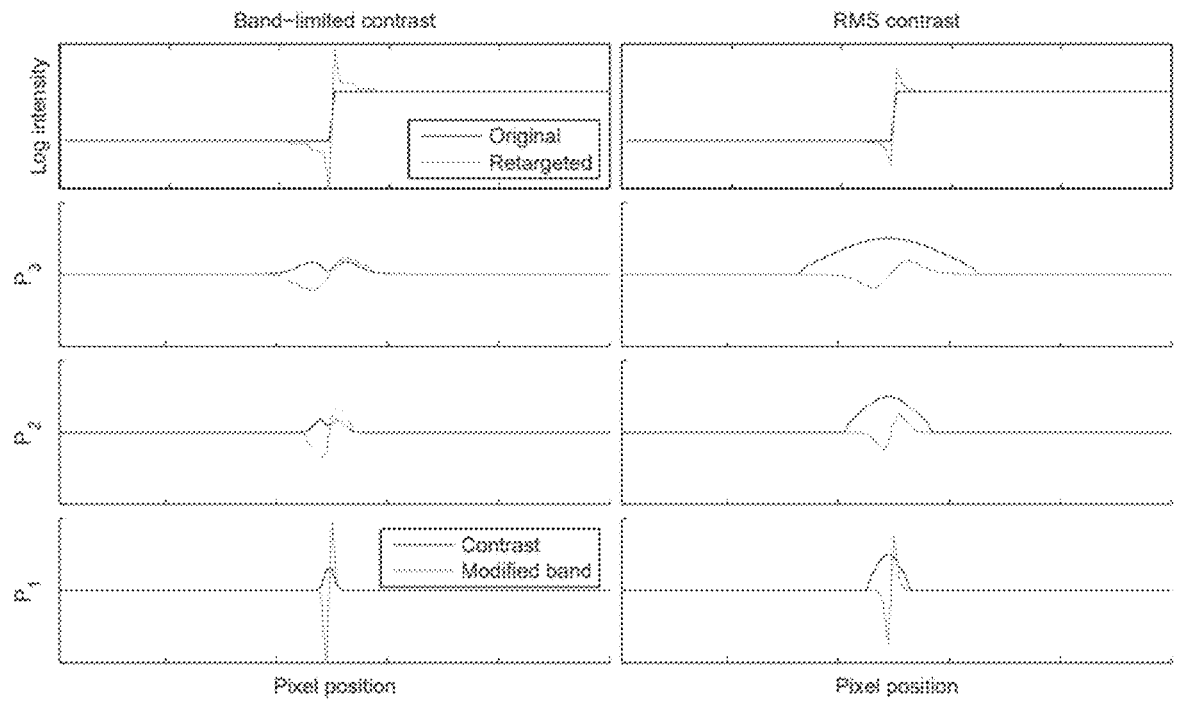
FIG. 9 illustrates the effects of contrast retargeting of an image edge feature according to various methods.

Sharp edge contrast features are decomposed into smaller band pass contrast components at several levels of the pyramid. These bandpass components are smaller than the total edge contrast and will be over-enhanced during retargeting to lower luminance level leading to errors in appearance mapping. This is visually illustrated in FIG. 9. In FIG. 9, an edge (solid line, top) is enhanced with the present local contrast retargeting method using either band-limited contrast (left) or RMS contrast (right). The plots labelled $P_k$ (k=1, 2, 3) show the band-pass or RMS contrast (dashed) and the signal (solid) in the band k after retargeting. Band-limited contrast underestimates the contrast of the edge and leads to excessive enhancement. RMS contrast can capture the contrast of an edge across the bands and does not cause over-enhancement. We employ a measure of contrast that integrates information from a plurality of, preferably all, frequencies in preferred embodiments, yet is localized and captures the contrast of a particular frequency band.

A measure of contrast that is commonly used for noise and broad-band patterns is the root-mean-square (RMS) contrast:

$$c_{RMS} = \sqrt{\int \left(\frac{\Delta Y(x)}{\bar{Y}}\right)^2 dx} = \sqrt{\int \left(\frac{Y(x) - \bar{Y}}{\bar{Y}}\right)^2 dx} \quad (12)$$

where Y and ΔY are the image luminance and increment at the position x, $\bar{Y}$ is the mean value, and the integral is computed over the entire image. The RMS contrast may be employed presently, however, it gives a single value per stimulus and is not very useful for complex images. Therefore, we preferably employ ways to localize this measure by restricting it to a local window, such as a Gaussian window. In order to relate the computed contrast measure to the logarithmic contrast, we preferably operate on the log-luminance image l=log(Y) rather than luminance itself. Hence, the localized broadband contrast can be calculated as:

$$c(x,y) = \sqrt{(g_\sigma * [l(x,y) - (g_\sigma * l)(x,y)]^2)(x,y)} \quad (13)$$

where * is the convolution operator and $g_\sigma$ is the Gaussian kernel with the standard deviation σ. The Gaussian window is preferably arranged to get smaller for higher frequencies to account for finer scale. This is preferably achieved by making it equal to half of the size of a single cycle at a particular frequency:

$$\sigma = 0.5 \frac{R_{ppd}}{\rho} \quad (14)$$

where $R_{ppd}$ is the angular display resolution in pixels per visual degree and ρ is the spatial frequency in cycles per degree. σ is given in pixels assuming a non-decimated Laplacian pyramid, where all levels have the same resolution. The frequency ρ can be computed as:

$$\rho = 2^{-(k+1)} R_{ppd} \quad (15)$$

where k=1, . . . , N is the level of the pyramid and k=1 denotes the finest level. Given the local contrast estimate, the contrast modification suitable to achieve an appearance match can be expressed as:

$$m_k(x, y) = \frac{c_k(x, y) - G(M_t) + G(\tilde{M}_t)}{c_k(x, y)} \quad (16)$$

where $c_k(x, y)$ is the contrast (Eq. 13) at the pixel location (x, y) and k-th level of the pyramid where k=1 . . . N. We select N so that the coarsest band (except the base band) has the peak frequency less or equal to 2 cpd. The function G is contrast measure conversion, given in Eq. 3. $M_t$ and $\tilde{M}_t$ are the detection thresholds for the input and retargeted images (Eq. 5).

In order to find these thresholds from the CSF, we preferably use the peak frequency corresponding to the given band (Eq. 14) and pixel luminance of the source (Y) and retargeted ($\tilde{Y}$) images. The latter is provided by the retargeted base-band image.

Figure 8:
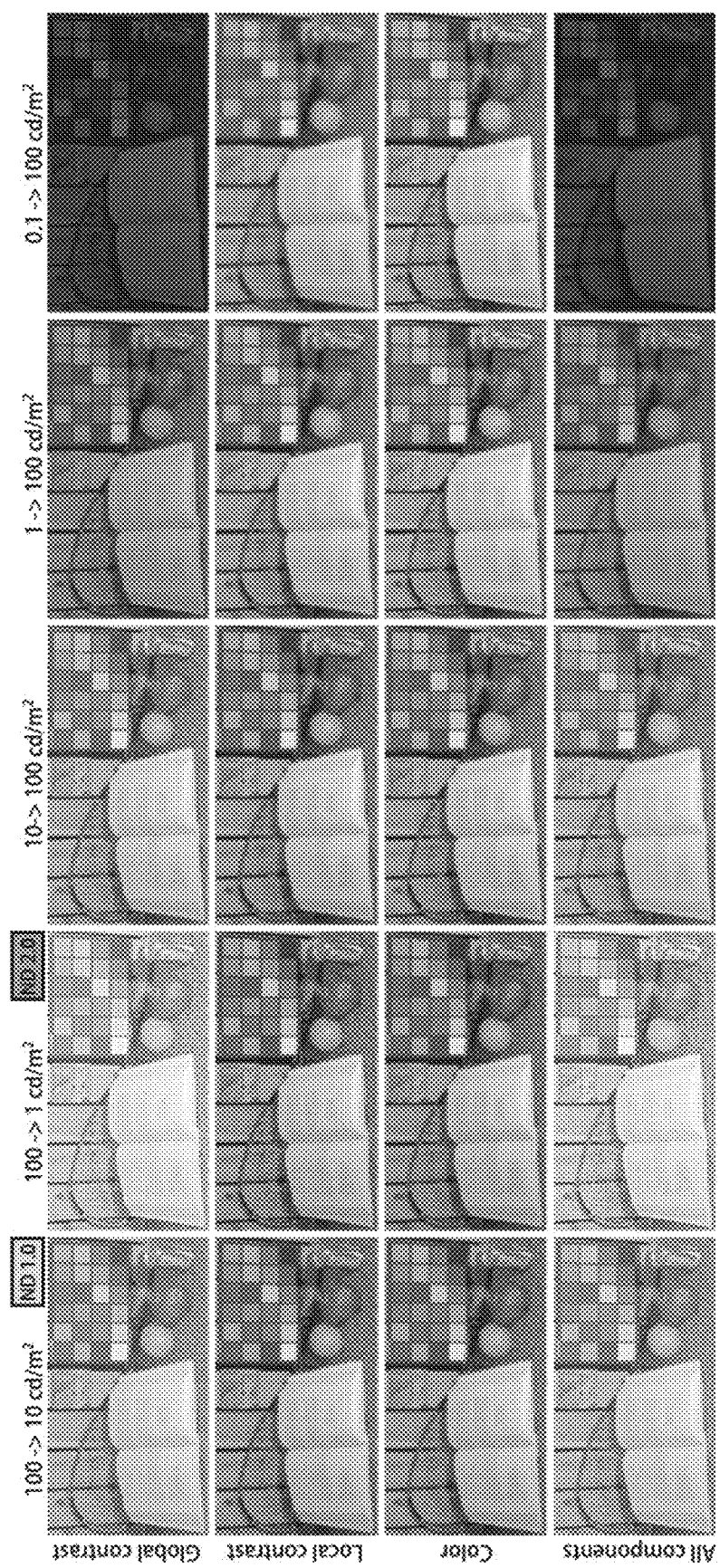
FIG. 8 illustrates adjusted images resulting from implementation of methods according to preferred embodiments of the invention.

Knowing the necessary modification, one may perform contrast retargeting as a local enhancement of the Laplacian pyramid:

$$\tilde{P}(x,y) = P_k(x,y) \cdot m_k(x,y) \quad (17)$$

where $P_k$ corresponds to the source image pyramid level. The low pass base band (k=N+1) is discarded. The resulting image may be reconstructed by summing all modified levels of the pyramid ($\tilde{P}_k(x, y)$) including the base band, which comes from the global contrast retargeting step (refer to FIG. 2). The result of the local contrast retargeting step isolated from other components of the method can be seen in the second row of FIG. 8. FIG. 8 shows results produced by different aspects of the invention, or different components of the composite method in a preferred embodiment. The top row of numbers indicate source and target peak luminance of a display. Note that the results for retargeting to a dark display on the left (100→10 and 100→1) are meant to be seen at much lower luminance levels though a neutral-density filter as shown next to the label on top. Much of the apparent artefacts, such as haloing and over-sharpening, disappear when seen through an ND filter. Note that the contrast is altered selectively depending on its magnitude. Such behaviour is consistent with the way we perceive contrast at different luminance levels.

Colour Retargeting

Reduced luminance affects not only luminance contrast but also colour. This is manifested by loss of colour saturation, mostly caused by reduced response of the cones, and the shift of hue towards more bluish colours, known as Purkinje shift. The latter effect is due to the fact that rods and cones share the same neural pathways to transmit their signal to the visual cortex [Cao et al. 2008]. In the photopic luminance range the information from the cones is the dominant signal, whereas in the scotopic range rods become dominant. In mesopic range, when both types of photoreceptor cells are active, the signal from the rods is combined with the signal from the cones in the early stages of visual processing. The variable contribution of the rod signal to the neural channel of each cone changes the ratio between the responses, resulting in the hue shift.

The goal is to find the resulting linear $[\tilde{R}\ \tilde{G}\ \tilde{B}]$ colour values with a hue shift given input linear values $[R\ G\ B]'$ and the target luminance Y.

We start by modelling the response of the photoreceptor, which is the product of spectral distribution of light reaching the retina, $L(\lambda)$, and spectral sensitivity of each type of photoreceptor: L-, M-, S-cones and rods, $\sigma^P(\lambda)$:

$$E_P(C) = \int_\lambda L(\lambda)\sigma_P(\lambda)d\lambda \tag{18}$$

where $\lambda$ is the wavelength and index P corresponds to the type of photoreceptor: L, M, S, or R. We use the normalized Smith & Pokorny cone fundamentals [Smith and Pokorny 1975] for the L-, M- and S-cone sensitivities and CIE 1951 scotopic luminous efficiency function for rods. Usually, the incoming light is described as the product of three or more spectral basis functions ($\pi$) and their coefficients (p):

$$L(\lambda) = \Sigma_{i=1}^{K} \Pi_i(\lambda)p_i \tag{19}$$

Figure 10:
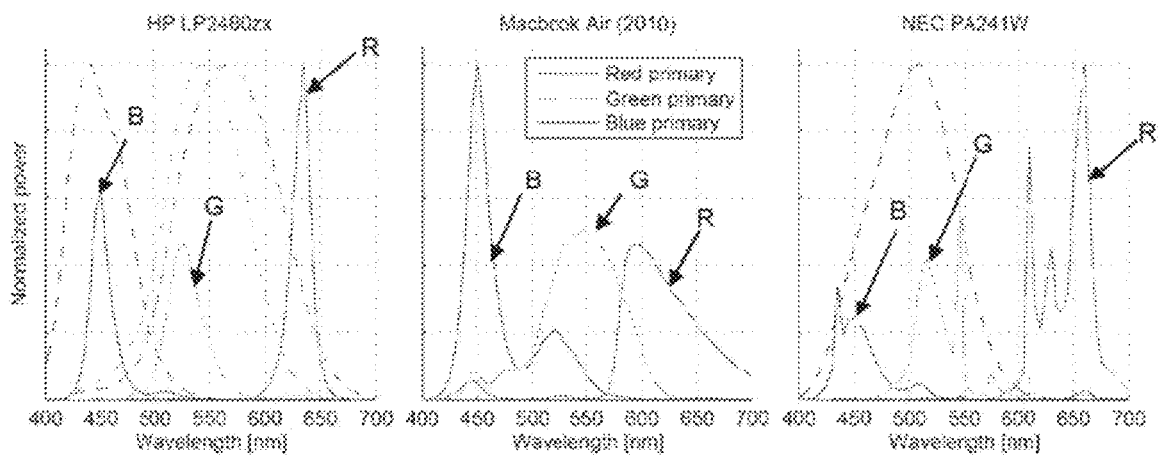
FIG. 10 illustrates spectral emissions of three different image display panels.

Without losing generality, we can simplify the model and assume that the coefficients $p_{1\ldots3}$ correspond to linear RGB colour values. In FIG. 10 we show the spectral primaries $\pi$ for several displays that we measured. This figure shows the spectral emission of the tested displays. The left plot also shows Smith & Pokorny cone fundamentals (dashed lines), and the right plots shows the CIE scotopic luminous efficiency function (dashed black). It is then possible to find a matrix $M_E$ for converting the linear RGB values into photoreceptor responses:

$$\begin{bmatrix} E_L \\ E_M \\ E_S \\ E_R \end{bmatrix} = M_E \begin{bmatrix} R \\ G \\ B \end{bmatrix} \tag{20}$$

where the coefficients of the matrix $M_E$ are given by:

$$m_{P,i} = \int_\lambda \Pi_i(\lambda)\sigma_P(\lambda)d\lambda \tag{21}$$

Cao et al. [Cao et al. 2008] observed that the rod signal shares the pathway with L-, M-, and S-cone signals and its influence is additive and depends on the luminance of the signal. The combined responses of each cone channel with the rod input, L, M and S, can be expressed as:

$$\begin{bmatrix} L \\ M \\ S \end{bmatrix} = \begin{pmatrix} 1 & 0 & 0 & k_1(Y) \\ 0 & 1 & 0 & k_1(Y) \\ 0 & 0 & 1 & k_2(Y) \end{pmatrix} \begin{bmatrix} E_L \\ E_M \\ E_S \\ E_R \end{bmatrix} = M_C(Y) \begin{bmatrix} E_L \\ E_M \\ E_S \\ E_R \end{bmatrix} \tag{22}$$

where $k_1(Y)$ and $k_2(Y)$ are the functions modelling rod input strength to the $L(k_1)$, $M(k_1)$ and $S(k_2)$ channels at luminance Y. These functions are obtained by interpolating between the values measured in [Cao et al. 2008] (the value of $k_2$ is scaled by 0.5 due to a similar scaling of the S channel response), which are listed in the table below.

| Y [cd/m²] | 10 | 0.62 | 0.10 |
|---|---|---|---|
| $k_1$ | 0 | 0.0173 | 0.173 |
| $k_2$ | 0 | 0.0101 | 0.357 |

The signal is then processed further down the visual cortex and combined into opponent colour space. However, since the transformation into the opponent colour space is linear, we can match the colours at this early stage. We assume that two colours at luminance Y and $\tilde{Y}$ will appear similar if their cone contrast relative cone response values are equal:

$$\begin{bmatrix} L \\ M \\ S \end{bmatrix} \cdot \frac{1}{Y} = \begin{bmatrix} \tilde{L} \\ \tilde{M} \\ \tilde{S} \end{bmatrix} \cdot \frac{1}{\tilde{Y}} \tag{23}$$

Note that, while it is very difficult, or impossible, to directly match LMS channels because of vastly different responses to a bright and dark display, we find that the cone contrast relative cone responses can be easily matched. After introducing Eq. 20 and 22 into Eq. 23, we can find the retargeted colour values from:

$$\begin{bmatrix} \tilde{R} \\ \tilde{G} \\ \tilde{B} \end{bmatrix} = \frac{\tilde{Y}}{Y}(M_C(\tilde{Y})M_E)^{-1}M_C(Y)M_E \begin{bmatrix} R \\ G \\ B \end{bmatrix} \tag{24}$$

Matching cone contrast allows the invention, in preferred embodiments, to correct for the hue shift. One may also account for the loss of colour saturation caused by decreasing sensitivity of the cones as well as changes introduced by the tone curve [Mantiuk et al. 2009]. We experimented with the complete model of [Cao et al. 2008], which introduces non-linear gains into opponent responses, but the results were unsatisfactory. The problem was caused by the fact that the model does not take into account the display specifications, which caused the results to frequently fall outside the available colour gamut if the peak luminance of the two display was significantly different. Instead, we found a simple saturation correction to work very well. After experimenting with saturation correction in CIE Lab, CIE Luv colour spaces and a luminance-preserving method [Mantiuk et al. 2009], we found that the best results are produced by the common tone-mapping colour correction formula:

$$\hat{R} = \left(\frac{\tilde{R}}{\tilde{Y}}\right)^{\frac{s(Y)}{s(\tilde{Y})}} \tilde{Y} \tag{25}$$

The same formula is applied to green and blue colour channels. The matching saturation function s(Y) was found in a matching experiment with a reference image shown at 200 cd/m² using the setup described herein.

Figure 11:
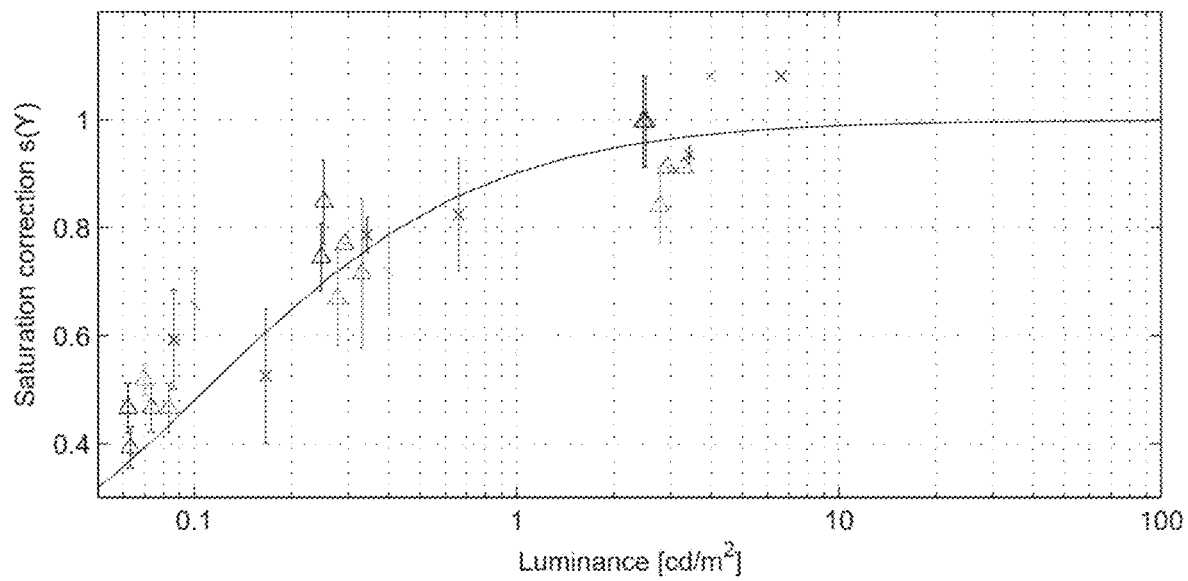
FIG. 11 illustrates a curve representing the change in a colour saturation correction according to luminance changes.

The results of the experiment are shown in FIG. 11 and the best fitted curve is given by:

$$s(Y) = \frac{Y}{(Y + k_3)} \quad (26)$$

where $k_3$ is equal to 0.108. The matching saturation factor is shown in this figure with changing mean luminance of an image. The black line is the fitted curve (Eq. 26). Error bars denote standard errors. The result of colour retargeting isolated from other components of the method can be seen in the third row of FIG. 8. Note that the hue changes due to Purkinje shift and loss of saturation at low luminance.

Summary

The method as described in preferred embodiments herein, takes as an input an image in linear RGB space and the specifications of 2 displays. A display model is applied to the image to determine its colourimetric properties when shown on one of the displays (forward display model step in FIG. 2). A global tone curve is calculated with regard to the output display specification (global contrast retargeting step) and it is applied to the original image. A Gaussian Pyramid is then calculated for this tone-corrected image and only its baseband is extracted. The original image is also decomposed into a Laplacian pyramid and the contrast at each layer other than baseband is altered to match the contrast as seen on the original display using Eq. 17 (local contrast retargeting step). Then, the base-band of the tone-mapped image is merged with all the layers, except the baseband, of the contrast-enhanced Laplacian pyramid. This results in an image with improved tone curve, corrected contrast and no halo effect. The colour changes caused by rod input and saturation are estimated based on the input and output luminance and the new linear RGB values are calculated using Eq. 24 and 25 (Colour retargeting step). Finally, an inverse display model of the second display is applied to produce the final image.

Because human vision does not retain the same contrast and colour perception across the luminance range, images need to be compensated when shown at a different luminance level than originally intended. The present method can provide such a compensation by retargeting night scenes for bright displays or retargeting bright scenes for a dark displays. The latter retargeting scenario allows for a novel application, in which an image is compensated for dark display, which leads to significant power saving in mobile devices while maintaining good image quality. Although many appearance models and tone-mapping operators claim to predict image appearance changes with luminance, we demonstrated (see FIG. 16) that none of the existing models accounts for all relevant effects and can produce acceptable results for a range of luminance retargeting scenarios. While typical image appearance models usually involve a pair of forward and inverse perceptual models, which differ in the selection of viewing conditions, we take a very different approach with an optimized tone curve. We bring from the field of vision science a simple but powerful contrast matching model, which has not been used in image and video applications before. The rod contribution to cone vision is used to predict Purkinje shift, and combined with the present new measurements to predict also colour saturation loss. Each component and the entire method is tested in experimental conditions to ensure a good appearance match.

Applications

Dark Display.

The primary application of the present method is to compensate the appearance changes seen when images are shown on much darker displays. Such compensation, shown in FIGS. 1 and 8, is in particular attractive for mobile devices that can reduce their backlight illumination when used in dark environment thereby reducing power consumption. We found that the peak luminance of a 1000:1 display can be reduced to as little as 1 $cd/m^2$. Further brightness reduction results in excessive loss of colour vision, which cannot be compensated. It is important to note that the compensation can take advantage of new display technologies, such as OLED, which offer much expanded colour gamut and contrast. Such extra gamut can reproduce the highly saturated colours and contrast that can be found in compensated images.

Age-Adaptive Compensation.

Figure 12:
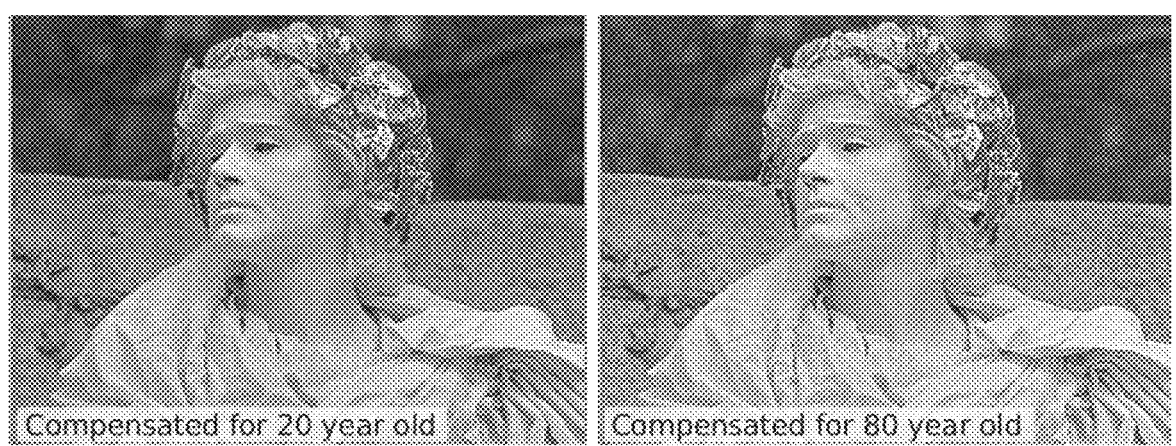
FIG. 12 illustrates an image compensated for viewing by younger (left) viewers and older (right) viewers.

Because the present method relies on a model of contrast sensitivity, it can be easily extended to account for the differences in acuity and sensitivity between young and elderly observers. In FIG. 12 we show image compensation for a dimmed 10 $cd/m^2$ peak luminance display tailored for 20-year old and 80-year old observers. In this figure, images are compensated for viewing on a 10 $cd/m^2$ peak luminance display, individually for younger and older observers. Typically little compensation is needed for 20-year old, but details and brightness must be boosted for the older observer.

Reproduction of Night Scenes.

Figure 13:
FIG. 13 illustrates a comparison of an original image (left), that image as adjusted according to existing methods (middle) and as adjusted according to the present invention (right)

The present method can also retarget images of night scenes to reproduce their appearance on much brighter displays. FIG. 8 shows examples of retargeting for a test scene and FIG. 13 (center) shows an example for a scene-referred HDR image. In this latter figure, best exposure from a scene-referred HDR image (left) is compared with a faithful reproduction of night vision (center) and exaggerated visualization for a more dramatic effect (right). Compare the differences in the visibility of details and colour. Please note that the loss of acuity in the cathedral image is visible only in darker image parts, as expected. Although a number of tone-mapping operators and appearance models are meant to predict such appearance change, none of the existing methods can accurately predict the full range of effects, as discussed in the next section.

Visualization of Night Scenes.

Figure 14:
FIG. 14 illustrates a comparison of an original image (left), that image as adjusted according to the present invention to represent a night view (middle) and as adjusted according to the present invention to represent a dramatic/exaggerated view (right)

The actual appearance change due to low luminance is often subtle and much smaller than predicted by many visual models. To achieve more dramatic effect in entertainment applications, where perceptual accuracy is not crucial, it is often desirable to alter the appearance above the level predicted by the visual model. This is shown in the right image of FIG. 14, where we adjusted parameters to show an excessive change of image appearance.

Visualization of Age-Related Vision Loss.

Figure 15:
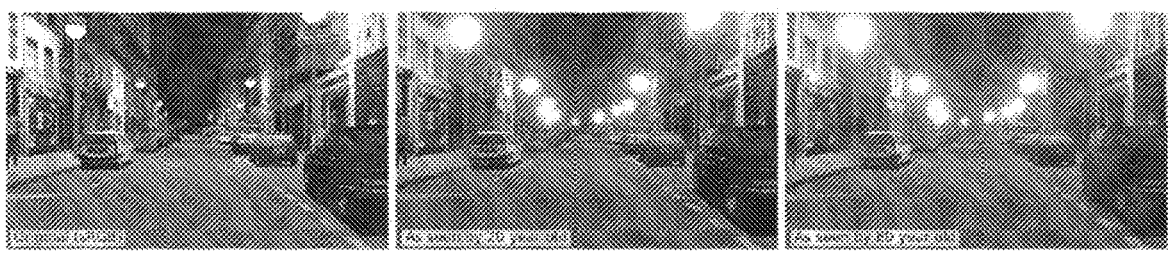
FIG. 15 illustrates a comparison of an original image (left), that image as adjusted according to existing methods (middle) and as adjusted according to the present invention (right)

Similarly as it is possible to target dark-display compensation for an age-group, it is also possible to account for the age when reproducing night scenes. In FIG. 15 we visualize a scene from a driving simulator, as seen by a 20- and 80-year-old observers. This figure shows a simulation of night vision for 20 and 80 year old observers. The simulation assumes compensated refraction and the age-related vision loss due to reduced retinal illuminance (senile miosis and crystalline lens aging), disability glare, and neural sensitivity loss. Notice the loss of fine details (when enlarged on a screen), such as the car license number, in the image on the right. The driving simulator rendering is the courtesy of LEPSIS (part of IFSTTAR). To complete visualization, we included in this application the age-dependent model of disability glare based on the CIE recommendation [Vos and van den Berg 1999].

Video.

When content-independent approach is used (S(l)=1 in Eq. 9), the present method does not contain any temporarily inconsistent components and video can be processed frame-by-frame. A content-dependent approach requires temporal tone-curve filtering, such as the one proposed in [Mantiuk et al. 2008]. Examples of retargeted video clips can be found in the supplementary materials.

Comparison with Other Methods

In this section we compare the present proposed method with several alternative techniques. CIECAM02 is the state-of-the-art colour appearance model, which accounts for a number of luminance-dependent effects, such as Hunt and Stevens effects. To retarget images, we process them through forward and then inverse CIECAM02 transforms. However, we vary the viewing-conditions-dependent parameters between the transforms. Depending on the source and target luminance levels, the viewing conditions vary between dark, dim and average. We also altered the luminance of the adapted white point to correspond to a drop in luminance levels, but we did not notice this parameter to have a significant effect on the results.

Figure 16:
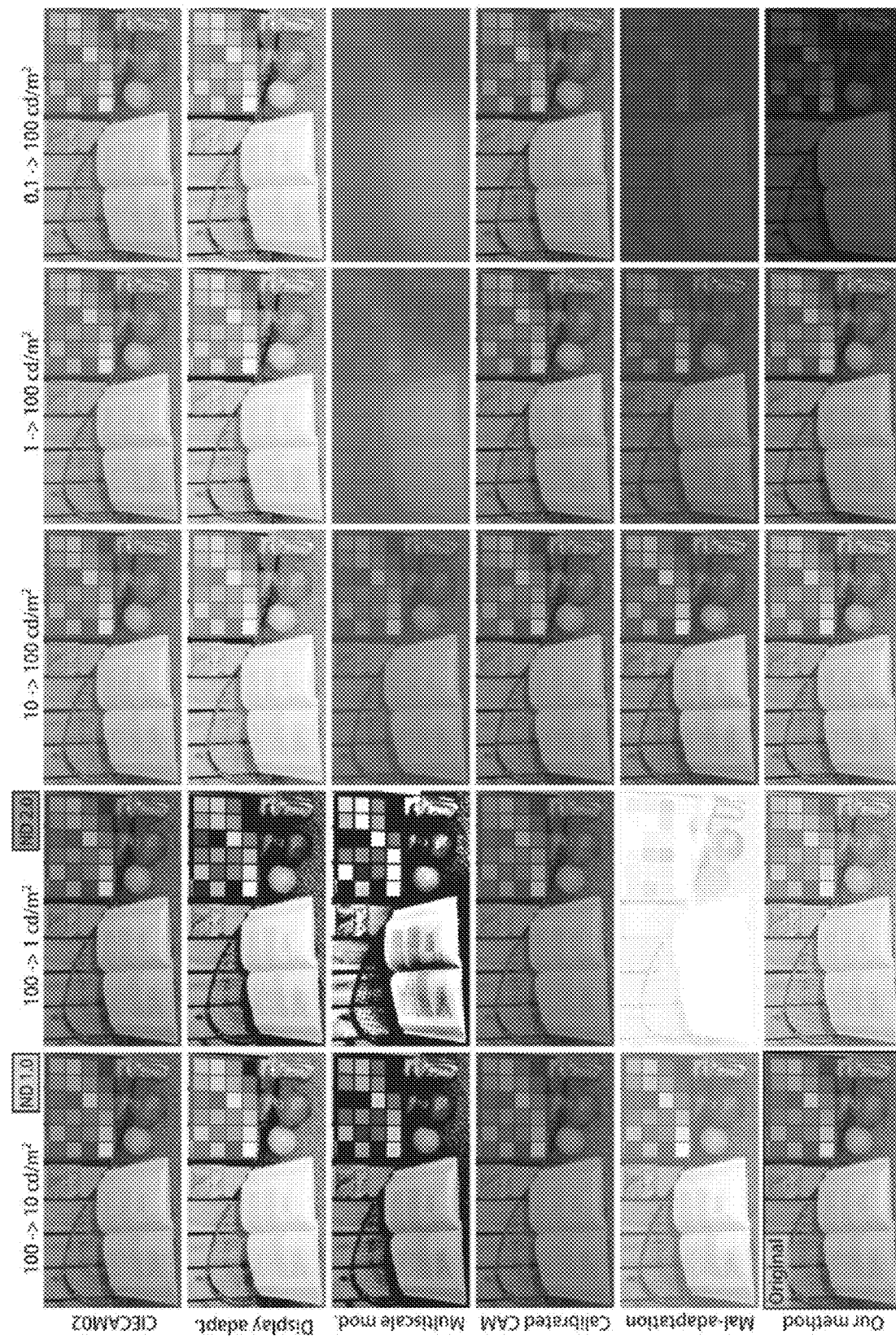
FIG. 16 illustrates a comparison of images as adjusted according to existing methods (first 5 rows) and as adjusted according to the present invention (bottom row)

FIG. 16 shows the results of different methods (rows) when retargeting from one luminance level to another (columns). Columns labels are the same as in FIG. 8. The original image in shown in the left-bottom corner instead of the 100→10 result for the present method, which can be found in FIG. 8.

As shown in the top row of FIG. 16, CIECAM02 predicts the loss of perceived contrast and colour saturation at low light and compensates for it by boosting overall image contrast at the cost of reducing brightness (100!1 cd/m2 scenario). As we show later, such images offer an inferior appearance match. The appearance changes due to very low luminance (1→100 cd/m$^2$ case) are too subtle, confirming that the model is in fact limited to the photopic vision.

Display adaptive tone-mapping [Mantiuk et al. 2008] is a tone mapping operator that accounts for the dynamic range and absolute luminance of the target display. The operator utilizes a tone-curve optimization similar to retargeting global contrast in the present method, though based on the transducer function. The operator is limited to global (spatially invariant) tone-curve, which cannot account for frequency-dependent and colour effects. We used the original implementation from the pfstools/pfstmo software. Similarly as CIECAM02, that algorithm correctly predicts the loss of contrast with luminance (second row in FIG. 16). However, it overpredicts the effect due to the transducer function. The colours that are too dark to be reproduced are clipped to black in the 100→1 scenario. The algorithm cannot retarget night scenes as it does not take into account the luminance of the input image.

Multi-scale model of adaptation, spatial vision and colour appearance [Pattanaik et al. 1998] is one of the most comprehensive models of the visual system, accounting for a large range of appearance phenomena. We reimplemented the algorithm with the help of partial code fragments published by the authors. The best results were achieved when the low-pass band of the target image was multiplied by a constant factor, which is the treatment recommended by the authors for low-dynamic range images.

The results shown in FIG. 16 demonstrate that the method predicts an extensive set of visual phenomena: loss of acuity, Purkinje colour shift, loss of colour saturation and contrast. However, it also clear that the magnitude of all these effects is not correctly predicted: the contrast and the acuity loss due to luminance is excessive, the colour cast due to Punkinje shift is too subtle. The result for 100→1 reveal another limitation, shared with most forward-inverse visual models: the resulting colours often exceed the available dynamic range, resulting in a non-reproducible image.

Calibrated image appearance reproduction model [Reinhard et al. 2012] combines the goals of tone-mappings and colour appearance to reproduce images on a range of display devices. We used the implementation provided by the authors and varied the input image luminance and display adaptation according to the source and target luminance levels. The algorithm produces pleasing results over a wide variety of high dynamic range images. However, as shown in the 4th row of FIG. 16 there is little change in image appearance regardless of the retargeting scenario. This suggests that the model does not account for luminance-dependent effects in the non-photopic luminance range.

Perceptual mal-adaptation model [Irawan et al. 2005] is a tone mapping operator that is capable of simulating loss of visibility experienced under changing illumination conditions. As shown in the fifth row in FIG. 16, the method can predict reduced contrast and brightness for dark scenes. However, it does not contain spatial processing that could simulate loss of acuity, nor does it account for hue and saturation changes. The operator does not produce usable results when compensating for a dark display (100→1 scenario).

Tone-mapping for low-light conditions [Kirk and O'Brien 2011] employs the same model of Cao et al. [2008] as the present method to simulate Purkinje shift. However, since the method assumes full adaptation to scotopic conditions across an image, it applies the same processing also to bright areas, which are seen by the photopic vision. The result is a bluish haze across the image shown in FIG. 15-center. FIG. 15 shows a comparison of the present method against a perceptual tone mapping for low light conditions [Kirk and O'Brien 2011]. The image is courtesy of Kirk and O'Brien. The present method applies the hue shift selectively, only in the dark regions, producing images that more closely resemble the perception of night scenes. The method of Kirk et al. also does not simulate acuity loss, loss of cone sensitivity and the change of perceived contrast.

The present method is the most comprehensive model of luminance effects on vision from all the presented methods. It takes a very different strategy to global contrast retargeting and finds a tone-curve that obeys the constraints of the target display dynamic range, so that the resulting image does not suffer from excessive clipping of pixel values. The colour cast due to Purkinje shift is visible, but only at low luminance levels. The local contrast modification does not simply sharpen or blur an image, but selectively reintroduces or removes image detail. The loss of acuity results in the loss of small contrast details while larger contrast is mostly unaffected. All these changes result in images that correspond to the actual image appearance when seen in the present experimental set up, described herein.

Experimental Comparison

To objectively confirm that the proposed method offers a better appearance match, we ran a pairwise comparison experiment. From the methods discussed in the previous section, we selected only those that produced acceptable results in a particular retargeting scenario. We included a "gamma" function with the exponents 1.5, as this is common practice for dark viewing conditions [Fairchild 2005, p. 125]. We also included the original unprocessed images as a control condition. The experimental setup was identical as the one described above, except that one portion of the screen contained two images, which were the result of two alternative retargeting methods. The observers were asked to choose the image that most closely matched the appearance of the image shown to the other eye when a 2.0D filter was worn on one eye or the other, depending on the scenario. Seventeen naive observers, who did not take part in the parameter adjustment experiments, compared the methods for eight scenes using the full pairwise design.

Results

Figure 17:
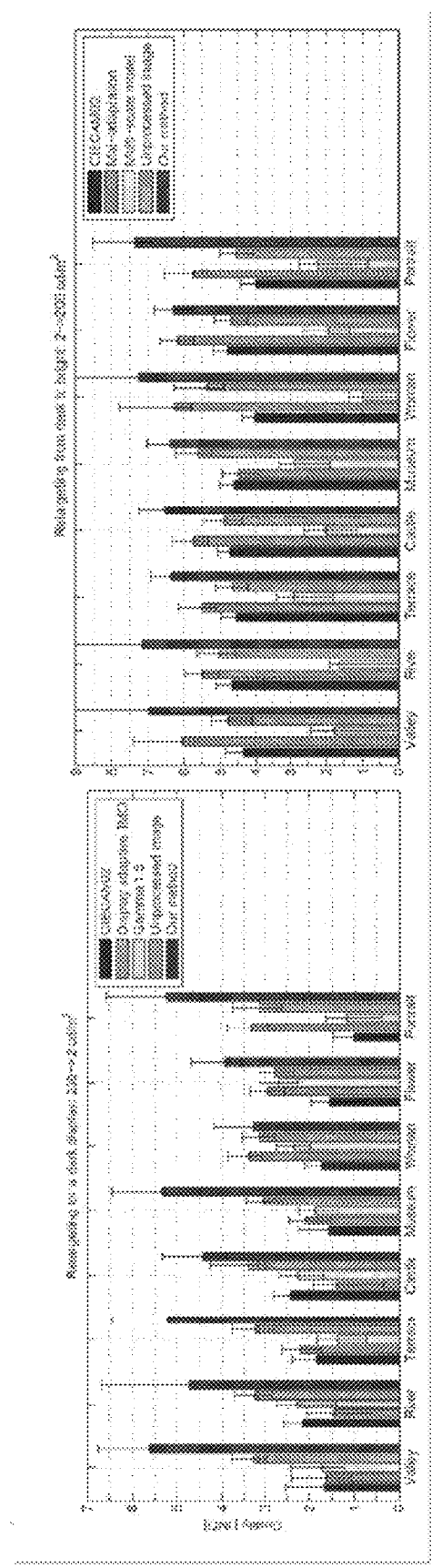
FIG. 17 illustrates a comparison of experimental data associated with the retargeting of a bright image for a dark display (left), a comparison of experimental data associated with the retargeting of a dark image for a bright display (right).

FIG. 17 shows the results of the pairwise comparison experiment scaled in JND units (the higher, the better) under Thurstone Case V assumptions, where 1 JND corresponds to 75% discrimination threshold. Note that absolute JND values are arbitrary and only relative differences are meaningful. The error bars denote 95% confidence intervals computed by bootstrapping.

In order to estimate what portion of the population selects one method as better than the other, the results were scaled in JND units using a similar method as in [Eilertsen et al. 2013]. The scaled results in FIG. 17 show that the present method was selected as providing a significantly better appearance match in almost all cases. Only in two cases, which were a portrait image Woman in the 200→2 scenario and Flower image in the 2→200 scenario, the present method was comparable to the second best, though the ranking is not statistically significant. Surprisingly, very few of the existing methods provided reproduction better than the original unprocessed image.

Even a contrast-enhancing gamma 1.5 seems to do more harm than good when retargeting for a dark display. Note, that we did not include the methods that did not work or failed in either retargeting scenario, such as a Display adaptive TMO in the 2→200 case and Mal-adaptation in the 200→2 case. These results clearly indicate that, unlike the existing algorithms, the present method can produce consistently good results for two very different retargeting scenarios.

The derivation of the present method was driven, calibrated and tested with strict experimental procedures to ensure a good appearance match between luminance levels. It is important to note that we did not assume correctness of the visual models from the literature, which were measured for simple stimuli. Instead, we tested them with complex images across a range of conditions. We found that a haploscopic matching method, where each eye is adapted to a different luminance level, gave the most consistent and repeatable results and therefore was used in all the present experiments.

Images were shown on a colourimetrically calibrated 24" 1920×1200 LCD display (NEC PA241W) and viewed in a dark room. The display was driven with 10 bits per colour channel and used the native extended colour gamut. A piece of black cardboard was used to separate the display screen into two halves, so that each eye could see only one half of the screen. The viewing distance was restricted to 85 cm and the pixel angular resolution was 56 pixels per degree. Observers wore modified welding goggles, in which we removed the protective filter for one eye and introduced a photographic neutral density (ND) filter (Kodak Wratten 96 1D and 2D) for the other eye. The choice of the eye to cover with the filter was randomized between the sessions. Such a setup ensured that both eyes were adapted separately to different luminance levels and the visual glare did not affect the "darker" eye. The observers were asked to adjust the parameters or make judgements so that the displayed image shown to the "dark" eye was as close as possible to the reference image shown to the "bright" eye (the method-of-adjustment).

Each parameter adjustment session was completed by at least three expert observers for 10 images from Kodak database1 and the results were averaged. The observers were excluded from the comparison experiment described above. We used Powell's conjugate direction method [Powell 1964] for finding minimum of multi-dimensional function to iterate over the parameters of the retargeting method. At least two full iterations were completed before the final parameter values were found.

REFERENCES

BARTEN, P. G. J. 1999. Contrast sensitivity of the human eye and its effects on image quality. SPIE Press.
BARTLESON, C. J., AND BRENEMAN, E. J. 1967. Brightness Perception in Complex Fields. Journal of the Optical Society of America 57, 7 (July), 953.
BERNS, R. S. 1996. Methods for characterizing crt displays. Displays 16, 4, 173-182.
BRADY, N., AND FIELD, D. J. 1995. What's constant in contrast constancy? The effects of scaling on the perceived contrast of bandpass patterns. Vision research 35, 6 (March), 739-56.
CAO, D., POKORNY, J., SMITH, V. C., AND ZELE, A. J. 2008. Rod contributions to color perception: linear with rod contrast. Vision research 48, 26 (November), 2586-92.
CHANG, N., CHOI, I., AND SHIM, H. 2004. DLS: Dynamic backlight luminance scaling of liquid crystal display. IEEE Transactions on Very Large Scale Integration (VLSI) Systems 12, 8.
EILERTSEN, G., WANAT, R., MANTIUK, R. K., AND UNGER, J. 2013. Evaluation of Tone Mapping Operators for HDR-Video. Computer Graphics Forum 32, 7 (October), 275-284.
FAIRCHILD, M. D. 2005. Color Appearance Models, 2nd ed. ed. John Wiley & Sons.
GEORGESON, B. Y. M. A., AND SULLIVAN, G. D. 1975. Contrast constancy: deblurring in human vision by spatial frequency channels. The Journal of Physiology 252, 627-656.
IRANLI, A., LEE, W., AND PEDRAM, M. 2006. Backlight dimming in power-aware mobile displays. In Proc. of the Annual Conference on Design Automation—DAC '06, ACM Press, New York, N.Y., USA, 604-607.
IRAWAN, P., FERWERDA, J., AND MARSCHNER, S. 2005. Perceptually based tone mapping of high dynamic range image streams. EGSR.
KANE, J. P., AND KURTZ, F. A., 2012. Adapting display color for low luminance conditions. Patent app. EP 2526688 A1.
KEROFSKY, L., AND DALY, S. 2006. Brightness preservation for LCD backlight dimming. Journal of the Society for Information Display 14, 12, 1111-1118.
KIRK, A. G., AND O'BRIEN, J. F. 2011. Perceptually based tone mapping for low-light conditions. ACM Transactions on Graphics 30, 4 (July), 1.
KUANG, J., JOHNSON, G., AND FAIRCHILD, M. 2007. iCAM06: A refined image appearance model for HDR image rendering. Journal of Visual Communication and Image Representation 18, 5, 406-414.
KULIKOWSKI, J. J. 1976. Effective contrast constancy and linearity of contrast sensation. Vision research 16, 12 (January), 1419-31.

MANTIUK, R., AND SEIDEL, H.-P. 2008. Modeling a generic tone-mapping operator. In Computer Graphics Forum, vol. 27, Wiley Online Library, 699-708.

MANTIUK, R., DALY, S., AND KEROFSKY, L. 2008. Display adaptive tone mapping. ACM Transactions on Graphics (Proc. of SIGGRAPH) 27, 3, 68.

MANTIUK, R., MANTIUK, R. K., TOMASZEWSKA, A., AND HEIDRICH, W. 2009. Color correction for tone mapping. Computer Graphics Forum (Proc. of Eurographics) 28, 2, 193-202.

MANTIUK, R., KIM, K. J., REMPEL, A. G., AND HEIDRICH, W. 2011. HDR-VDP-2: A calibrated visual metric for visibility and quality predictions in all luminance conditions. ACM Trans. Graph (Proc. SIGGRAPH) 30, 4 (July), 1.

MORONEY, N., FAIRCHILD, M., HUNT, R., LI, C., LUO, M., AND NEWMAN, T. 2002. The CIECAM02 color appearance model. In Proc. IS&T/SID 10th Color Imaging Conference, Society for Imaging Science and Technology, 23-27.

PATTANAIK, S. N., FERWERDA, J. A., FAIRCHILD, M. D., AND GREENBERG, D. P. 1998. A multiscale model of adaptation and spatial vision for realistic image display. In Proc. of SIGGRAPH '98, 287-298.

PELI, E. 1990. Contrast in complex images. Journal of the Optical Society of America A 7, 10 (October), 2032-2040.

PETIT, J., AND MANTIUK, R. K. 2013. Assessment of video tone mapping: Are cameras S-shaped tone-curves good enough? Journal of Visual Communication and Image Representation 24, 1020-1030.

POWELL, M. J. 1964. An efficientmethod for finding theminimum of a function of several variables without calculating derivatives. The computer journal 7, 2, 155-162.

REINHARD, E., POULI, T., KUNKEL, T., LONG, B., BALLESTAD, A., AND DAMBERG, G. 2012. Calibrated image appearance reproduction. ACM Transactions on Graphics 31, 6 (November), 1.

SMITH, V. C., AND POKORNY, J. 1975. Spectral sensitivity of the foveal cone photopigments between 400 and 500 nm. Vision Research 15, 2, 161-171.

THOMPSON, W., SHIRLEY, P., AND FERWERDA, J. 2005. A spatial post-processing algorithm for images of night scenes. Journal of Graphics Tools, 1-11.

VOS, J. J., AND VAN DEN BERG, T. J. 1999. CIE 135/1-6 Disability Glare. Tech. rep. WITKIN, A. 1984. Scale-space filtering: A new approach to multiscale description. In IEEE Int. Conf. on Acoustics, Speech, and Signal Processing, Institute of Electrical and Electronics Engineers, vol. 9, 150-153.

The invention claimed is:

1. A method for transforming an image of a first luminance to adjust a perceived color hue thereof for display by a display device according to a second luminance, the method comprising:
calculating a color hue adjustment factor for adjusting color values of an original image; and,
adjusting said color values of the original image according to the color hue adjustment factor thereby to provide a transformed image for display by said display device at said second luminance;
wherein said calculating includes representing numerically a cone photoreceptor response to said color values in terms of a corresponding contributory rod photoreceptor response at the second luminance.

2. The method according to claim 1, wherein said cone photoreceptor response per unit luminance at said second luminance is constrained to substantially match the cone photoreceptor response per unit luminance at said first luminance.

3. The method according to claim 1, wherein said contributory rod photoreceptor response is a luminance-dependent value added to said cone photoreceptor responses.

4. The method according to claim 2, wherein said contributory rod photoreceptor response is a luminance-dependent value added to said cone photoreceptor responses.

5. The method according to claim 1, wherein said representing numerically a cone photoreceptor response includes separately representing the individual responses of L-cones, M-cones and S-cones each in terms of a respective corresponding contributory rod photoreceptor response to luminance.

6. The method according to claim 1, wherein said color values are trichromatic color values.

7. The method according to claim 1, further comprising:
calculating a color saturation adjustment transform for further adjusting color values of the transformed image already transformed according to the color hue adjustment factor; and
further adjusting the color values ($\tilde{X}$) of the transformed image according to the color saturation transform thereby to provide a further transformed image for display by said display device at said second luminance;
wherein a given adjusted color value ($\hat{X}$) of the further transformed image is defined according to the value of the first luminance (Y) and the value of the second luminance ($\tilde{Y}$) and a saturation correction factor (s( . . . )) in accordance with the following transform:

$$\hat{X} = \tilde{Y} \times \left(\frac{\tilde{X}}{\tilde{Y}}\right)^{\frac{s(Y)}{s(\tilde{Y})}}$$

wherein the saturation correction factor is a function of luminance and approaches a value of zero as the value of luminance approaches zero and monotonically approaches a value of one (1.0) asymptotically as luminance increases.

8. A method according to claim 7, wherein said color values ($\tilde{X}$) of the transformed image are trichromatic color values.

9. A method for transforming an image having a first luminance to adjust a color saturation thereof for display by a display device having a second luminance, the method comprising:
calculating a color saturation adjustment transform for adjusting color values of an original image; and,
adjusting said color values ($\tilde{X}$) of the original image according to the color saturation transform thereby to provide a transformed image for display by said display device at said second luminance;
wherein a said adjusted color value is defined according to the value of the first luminance (Y) and the value of the second luminance ($\tilde{Y}$) and a saturation correction factor (s( . . . )) in accordance with the following transform:

$$\hat{X} = \tilde{Y} \times \left(\frac{\tilde{X}}{\tilde{Y}}\right)^{\frac{s(Y)}{s(\tilde{Y})}}$$

wherein the saturation correction factor is a function of luminance and approaches a value of zero as the value of luminance approaches zero and monotonically approaches a value of one (1.0) asymptotically as luminance increases.

10. The method of claim 9, further comprising determining an average luminance of said original image having said first luminance and determining an average luminance of said image having said first luminance, determining a respective value of said saturation correction factor (s(Y)) according to each said average luminance and adjusting said color values using said respective values of the saturation correction factor.

11. Apparatus for transforming an image of a first luminance to adjust a perceived color hue thereof for display by a display device according to a second luminance, the apparatus comprising:
a first calculating unit for calculating a color adjustment factor for adjusting color values of an original image; and,
a first adjuster unit for adjusting said color values of the original image according to the color adjustment factor thereby to provide a transformed image for display by said display device at said second luminance;
wherein said first calculating unit is arranged to represent numerically a cone photoreceptor response to said color values in terms of a corresponding contributory rod photoreceptor response a second luminance.

12. Apparatus according to claim 11, wherein said cone receptor response per unit luminance at said second luminance is constrained to substantially match the cone photoreceptor response per unit luminance at said first luminance.

13. Apparatus according to claim 11, wherein said contributory rod photoreceptor response is a luminance-dependent value represented as an addition to said cone photoreceptor responses.

14. Apparatus according to claim 12, wherein said contributory rod photoreceptor response is a luminance-dependent value represented as an addition to said cone photoreceptor responses.

15. Apparatus according to claim 11, wherein said calculating unit is arranged to represent numerically a cone photoreceptor response by separately representing the individual responses of L-cones, M-cones and S-cones each in terms of a respective corresponding contributory rod photoreceptor response to luminance.

16. Apparatus according to claim 11, wherein said color values are trichromatic color values.

17. Apparatus according to claim 11, further comprising:
a second calculating unit for calculating a color saturation adjustment transform for further adjusting color values of the transformed image already transformed according to the color hue adjustment factor; and
a second adjuster unit for further adjusting the color values ($\tilde{X}$) of the transformed image according to the color saturation transform thereby to provide a further transformed image for display by said display device at said second luminance;
wherein a given adjusted color value ($\tilde{X}$) of the further transformed image is defined according to the value of the first luminance (Y) and the value of the second luminance ($\tilde{Y}$) and a saturation correction factor (s( . . . )) in accordance with the following transform:

$$\hat{X} = \tilde{Y} \times \left(\frac{\tilde{X}}{\tilde{Y}}\right)^{\frac{s(Y)}{s(\tilde{Y})}}$$

wherein the saturation correction factor is a function of luminance and approaches a value of zero as the value of luminance approaches zero and monotonically approaches a value of one (1.0) asymptotically as luminance increases.

18. Apparatus according to claim 17 wherein said color values ($\tilde{X}$) of the transformed image are trichromatic color values.

19. Apparatus for transforming an image having a first luminance to adjust a color saturation thereof for display by a display device having a second luminance, comprising:
a calculating unit for calculating a color saturation adjustment transform for adjusting color values of an original image; and,
an adjuster unit for adjusting said color values ($\tilde{X}$) of the original image according to the color saturation transform thereby to provide a transformed image for display by said display device at said second luminance;
wherein said adjuster unit is arranged to adjust a said color value according to the value of the first luminance (Y) and the value of the second luminance ($\tilde{Y}$) and a saturation correction factor (s( . . . )) in accordance with the following transform:

$$\hat{X} = \tilde{Y} \times \left(\frac{\tilde{X}}{\tilde{Y}}\right)^{\frac{s(Y)}{s(\tilde{Y})}}$$

wherein the saturation correction factor is a function of luminance and approaches a value of zero as the value of luminance approaches zero and monotonically approaches a value of one (1.0) asymptotically as luminance increases.

20. Apparatus according to claim 19 wherein the calculating unit is arranged to determine an average luminance of said original image having said first luminance and to determine an average luminance of said image having said first luminance, and to determine a respective value of said saturation correction factor (s( . . . )) according to each said average luminance and to adjust said color values using said respective values of the saturation correction factor.

* * * * *